United States Patent [19]

Carpino et al.

[11] Patent Number: 5,789,415
[45] Date of Patent: Aug. 4, 1998

[54] AZACYCLIC-HETEROCYCLIC COMPOUNDS AS ANGIOTENSION II RECEPTOR ANTAGONISTS

[75] Inventors: Philip A. Carpino, Groton; Eric R. Larson, Stonington; Banavara L. Mylari, Waterford, all of Conn.

[73] Assignee: Pfizer Inc., New York, N.Y.

[21] Appl. No.: 569,133

[22] PCT Filed: Jul. 1, 1994

[86] PCT No.: PCT/IB94/00187

§ 371 Date: Jan. 11, 1996

§ 102(e) Date: Jan. 11, 1996

[87] PCT Pub. No.: WO95/02596

PCT Pub. Date: Jan. 26, 1995

Related U.S. Application Data

[63] Continuation of Ser. No. 92,349, Jul. 15, 1993, abandoned.

[51] Int. Cl.$^6$ .................... A61K 31/44; A61K 31/505; C07D 403/12; C07D 403/14

[52] U.S. Cl. .................... 514/256; 514/303; 514/341; 514/397; 549/79; 546/118; 546/275.1; 544/333; 548/315.1

[58] Field of Search .................... 544/284, 333; 546/118, 275.1; 549/79; 514/256, 303, 341, 397; 548/315.1

[56] References Cited

U.S. PATENT DOCUMENTS

| | | | |
|---|---|---|---|
| 5,240,928 | 8/1993 | Allen et al. | 514/259 |
| 5,283,242 | 2/1994 | Ellingboe | 514/186 |
| 5,300,668 | 4/1994 | Jardine | 556/441 |
| 5,308,853 | 5/1994 | Hodges | 514/336 |
| 5,350,752 | 9/1994 | Poss et al. | 514/259 |
| 5,387,592 | 2/1995 | Bradbury et al. | 514/312 |
| 5,521,206 | 5/1996 | Muller et al. | 514/400 |
| 5,583,141 | 10/1996 | Naka et al. | 514/303 |

FOREIGN PATENT DOCUMENTS

| | | |
|---|---|---|
| 0508723 | 10/1992 | European Pat. Off. |
| 0513533 | 11/1992 | European Pat. Off. |
| 0513979 | 11/1992 | European Pat. Off. |
| 0520423 | 12/1992 | European Pat. Off. |
| 0520723 | 12/1992 | European Pat. Off. |
| 0520724 | 12/1992 | European Pat. Off. |
| 0543491 | 5/1993 | European Pat. Off. |
| 9112001 | 8/1991 | WIPO |

Primary Examiner—Matthew V. Grumbling
Attorney, Agent, or Firm—Peter C. Richardson; Gregg C. Benson; A. Dean Olson

[57] ABSTRACT

Compounds of the formula

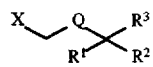

wherein:

Q is naphthyl, heterocyclic or heterobicyclic; $R^1$ and $R^2$, when taken separately, are hydrogen, hydroxy, alkyl, alkylthio, alkylsulfinyl, alkylsulfonyl, phenyl, heterocyclic or heterobicyclic; $R^1$ and $R^2$, when taken together, form a carbocyclic, carbobicyclic, heterocyclic or heterobicyclic group; $R^3$ is —$(CH_2)_nCOR^4$, tetrazolyl, alkyltetrazolyl, triazolyl, alkyltriazolyl, —$(CH_2)_nCH_2OH$, —$SO_2R^4$, —$SO_2NR^5R^6$ or —$NHSO_2R^7$; $R^4$ is hydrogen, hydroxy, —$NR^5R^6$, —$NHSO_2R^7$, alkoxy, alkylthio, —$NR^5R^6$, —$NHSO_2R^7$ or —OY; n is 0 to 5; Y is a pharmaceutically acceptable cation or a group hydrolyzable under physiological conditions; $R^5$ and $R^6$, when taken separately, are hydrogen, alkyl, —CONRR, —COOR or —$CO(C_6H_5)$; $R^5$ and $R^6$, when taken together, form an azacyclic ring; $R^7$ is alkyl or phenyl; each R is hydrogen or alkyl and X is an azacyclic or azabicyclic group, inhibit angiotensin II in mammals and are useful in treating conditions such as hypertension, congestive heart failure and glaucoma and as the active ingredient in pharmaceutical compositions for treating such conditions.

13 Claims, No Drawings

AZACYCLIC-HETEROCYCLIC COMPOUNDS AS ANGIOTENSION II RECEPTOR ANTAGONISTS

This application was filed under 35 U.S.C. §371 based on PCT/IB94/00187, which was filed on Jul. 1, 1994 which is a continuation of U.S. application Ser. No. 08/092,349 which was filed on Jul. 15, 1993 and is now abandoned.

BACKGROUND OF THE INVENTION

This invention relates to a certain class of azacyclic-heterocyclic compounds which have utility as regulators of the action of angiotensin II (AII), mediated by the AII receptor, in mammals, including humans, and accordingly, are useful in the treatment of hypertension, congestive heart failure, glaucoma and other conditions for which the action of AII is implicated. This invention relates also to pharmaceutical compositions containing these compounds, methods of inhibiting AII in mammals by administration of such compounds and also to certain intermediates in the preparation of such compounds.

The renin-angiotensin system (RAS) acts as a crucial regulatory mechanism in the control of homeostasis and fluid/electrolyte balance in mammals, including humans. Consequently, RAS activity has a direct influence on blood pressure and has been found to play an important role in congestive heart failure and in the development and maintenance of hypertension. Additionally, AII activity has been implicated in the development of elevated intraocular pressure, for example, as caused by glaucoma. AII, an octapeptide hormone produced via the cleavage of angiotensin I (AI) by angiotensin converting enzyme (ACE), is a potent and direct arterial vasoconstrictor, thereby effecting an increase in vascular resistance and blood pressure. AII is also known to stimulate the release of aldosterone, resulting in vascular congestion and hypertension by promoting the retention of sodium and fluids. The present invention concerns the potential beneficial effects of regulating the actions of AII which are mediated by the AII receptor.

Various azacyclic-benzyl-derived compounds have been described as AII antagonists. For example, see D. J. Carini et al., *J. Med. Chem.*, 33,1330-6 (1990), U.S. Pat. No. 4,207,324, EP 399731, EP 399732, EP 411766 A1, EP 412594 A2 and WO 91/11999.

SUMMARY OF THE INVENTION

The present invention relates to a class of compounds, and their pharmaceutically acceptable salts, having the formula

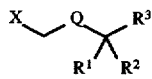

wherein:

Q is naphthyl, a 5 to 7 member heterocycle having from 1 to 3 atoms independently selected from nitrogen, oxygen and sulfur, or an 8 to 11 member heterobicycle having from 1 to 4 atoms selected from nitrogen, oxygen and sulfur, said heterocycle or heterobicycle being saturated, partially saturated or unsaturated and said naphthyl, heterocycle or heterobicycle optionally substituted with 1 to 4 $W^1$ substituents;

each $W^1$ substituent is independently selected from halo, hydroxy, nitro, cyano, $C_1$ to $C_8$ alkyl, $C_3$ to $C_7$ cycloalkyl, $C_1$ to $C_7$ alkoxy, amino, $C_1$ to $C_7$ alkylamino, di($C_1$ to $C_7$ alkyl)amino, $C_1$ to $C_7$ alkylthio, $C_1$ to $C_7$ alkylsulfinyl, $C_1$ to $C_7$ alkylsulfonyl, —CONRR, —COOR and phenyl, said alkyl, cycloalkyl, alkoxy, alkylamino, dialkylamino, alkylthio, alkylsulfinyl and alkylsulfonyl optionally substituted with 1 or more $W^2$ substituents, and said phenyl optionally substituted with 1 or more $W^3$ substituents;

each R is independently hydrogen or $C_1$ to $C_8$ alkyl, said alkyl optionally substituted with 1 or more $W^2$ substituents;

each $W^2$ substituent is independently selected from halo, hydroxy, oxo, $C_3$ to $C_7$ cycloalkyl, $C_1$ to $C_7$ alkoxy, acyloxy, phenyl and 5 to 7 member heterocycle having 1 to 3 atoms selected from nitrogen, oxygen and sulfur, said phenyl and heterocycle optionally substituted with 1 or more $W^3$ substituents;

each $W^3$ substituent is independently selected from halo, hydroxy, nitro, $C_3$ to $C_7$ cycloalkyl, $C_1$ to $C_7$ alkoxy, amino, $C_1$ to $C_7$ alkylamino, di($C_1$ to $C_7$ alkyl)amino, $C_1$ to $C_7$ alkylthio, $C_1$ to $C_7$ alkylsulfinyl and $C_1$ to $C_7$ alkylsulfonyl;

$R^1$ and $R^2$, when taken separately, are each independently selected from hydrogen, hydroxy, $C_1$ to $C_{10}$ alkyl, $C_1$ to $C_7$ alkylthio, $C_1$ to $C_7$ alkylsulfinyl, $C_1$ to $C_7$ alkylsulfonyl, phenyl and 5 to 7 member heterocycle or 8 to 11 member heterobicycle, having 1 to 3 atoms selected from nitrogen, oxygen and sulfur, said alkyl, alkylthio, alkylsulfinyl and alkylsulfonyl optionally substituted with 1 or more $W^4$ substituents, said phenyl and said heterocycle and heterobicycle optionally substituted with 1 to 5 $W^3$ substituents, wherein the $W^3$ substituents are as defined above, and said heterocycle being saturated, partially saturated or unsaturated, provided that $R^1$ and $R^2$ are not both hydroxy;

$R^1$ and $R^2$, when taken together with the carbon atom to which they are attached, form a $C_3$ to $C_7$ carbocyclic, $C_7$ to $C_{11}$ carbobicyclic, 3 to 7 member heterocyclic group having from 1 to 3 atoms independently selected from nitrogen, oxygen and sulfur, or a 7 to 11 member heterobicyclic group having from 1 to 4 atoms independently selected from nitrogen, oxygen and sulfur, said carbocyclic, carbobicyclic, heterocyclic or heterobicyclic group being saturated, partially saturated or unsaturated and optionally substituted with 1 or more $W^5$ substituents;

each W4 substituent is independently selected from halo, $C_3$ to $C_8$ cycloalkyl, phenyl and 5 to 7 member heterocycle having 1 to 3 atoms selected from nitrogen, oxygen and sulfur, said phenyl and heterocycle optionally substituted with 1 or more substituents independently selected from halo, hydroxy, nitro, $C_1$ to $C_{10}$ alkyl, $C_3$ to $C_7$ cycloalkyl, $C_1$ to $C_7$ alkoxy, amino, $C_1$ to $C_7$ alkylamino and di($C_1$ to $C_7$ alkyl)amino;

each $W^5$ substituent is independently selected from halo, hydroxy, nitro, cyano, oxo, $C_1$ to $C_8$ alkyl, $C_3$ to $C_7$ cycloalkyl, $C_1$ to $C_7$ alkoxy, amino, $C_1$ to $C_7$ alkylamino, di($C_1$ to $C_7$ alkyl)amino, $C_1$ to $C_7$ alkylthio, $C_1$ to $C_7$ alkylsulfinyl, $C_1$ to $C_7$ alkylsulfonyl, —CONRR, —COOR and phenyl, said alkyl, cycloalkyl, alkoxy, alkylamino, dialkylamino, alkylthio, alkylsulfinyl and alkylsulfonyl groups optionally substituted with 1 or more $W^2$ substituents, and said phenyl optionally substituted with 1 or more $W^3$ substituents, wherein the $W^3$ substituents are as defined above;

$R^3$ is —$(CH_2)_nCOR^4$, tetrazolyl, $C_1$ to $C_5$ alkyltetrazolyl, triazolyl, $C_1$ to $C_5$ alkyltriazolyl, —$(CH_2)_nCH_2OH$, —$SO_2R^4$, —$SO_2NR^5R^6$ or —$NHSO_2R^7$;

$R^4$ is hydrogen, hydroxy, —$NHSO_2R^7$, $C_1$ to $C_{10}$ alkoxy, $C_1$ to $C_7$ alkylthio, —$NR^5R^6$, —$NHSO_2R^7$ or —OY, said alkoxy and alkylthio groups optionally substituted with 1 or more $W^6$ substituents;

n is an integer from 0 to 5;

Y is a pharmaceutically acceptable cation or a group hydrolyzable under physiological conditions;

$R^5$ and $R^6$, when taken separately, are each independently hydrogen, hydroxy, cyano, $C_1$ to $C_{10}$ alkyl, $C_1$ to $C_8$ alkoxy, —COR, —CONRR, —COOR, phenoxy, —CO(C₆H₅) or 5 to 6 member heterocycle having 1 to 4 atoms selected from nitrogen, oxygen and sulfur, wherein R is as defined above, said alkyl optionally substituted with 1 or more $W^3$ substituents, wherein the $W^3$ substituents are as defined above, said —CO(C₆H₅) optionally substituted with 1 to 3 $W^6$ substituents and said heterocycle optionally substituted with 1 or more $W^5$ substituents, wherein the $W^5$ substituents are as defined above;

$R^5$ and $R^6$, when taken together with the nitrogen atom to which they are attached, form a 3 to 7 member ring having 1 to 3 nitrogen atoms and from 0 to 3 atoms selected from oxygen and sulfur, said ring being saturated, partially saturated or unsaturated and optionally substituted with 1 or more $W^1$ substituents, wherein the $W^1$ substituents are as defined above;

$R^7$ is $C_1$ to $C_{10}$ alkyl or phenyl, said alkyl optionally substituted with 1 or more $W^6$ substituents, and said phenyl optionally substituted with 1 or more $W^3$ substituents, wherein the $W^3$ substituents are as defined above;

X is an azacyclic group of the formula

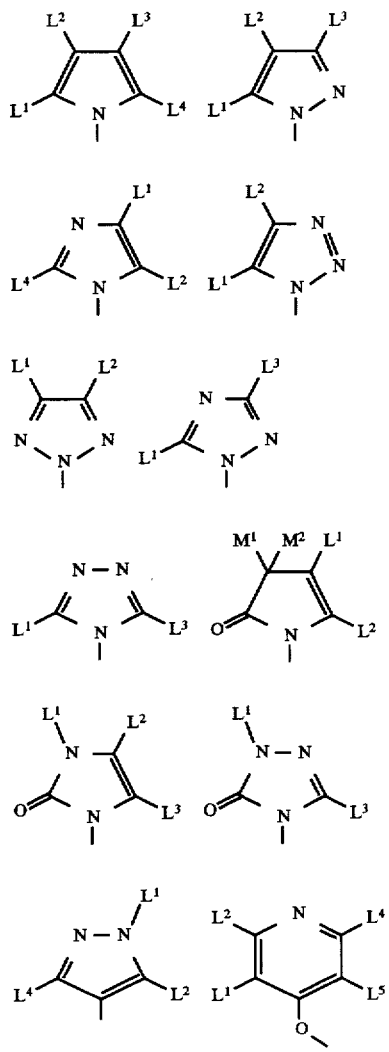

-continued

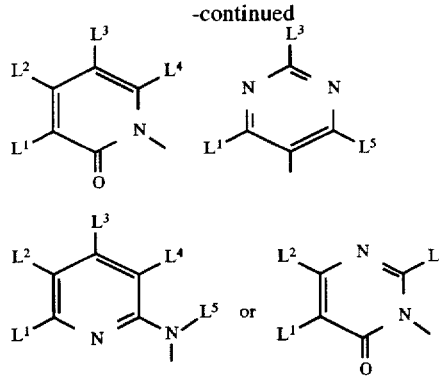

$L^1$, $L^2$, $L^3$, $L^4$ and $L^5$, when taken separately, are independently hydrogen, halo, nitro, $C_1$ to $C_6$ alkyl, $C_3$ to $C_7$ cycloalkyl, polyfluoro-$C_1$ to $C_4$ alkyl, aryl, heteroaryl, tetrazol-5-yl, —COR⁸, —CO₂R⁸, —CONHSO₂R⁹, —CONR¹⁰R¹⁰, —CONH(tetrazol-5-yl), —OR⁹, —OCONR⁹R¹¹, —NR⁸R⁹, —NHCOR⁹, —NHCO₂R⁹, —NHCONR⁸R⁹, —NHSO₂R⁹, —NHSO₂NR⁹R¹¹, —NHSO₂-polyfluorophenyl, —SR⁹, —SOR⁹, —SO₂R⁹, —SO₂NHCN, —SO₂NR¹¹R¹², —SO₂NHCOR⁹, —SO₂NH-heteroaryl, —PO(OR⁸)₂ or —PO(OR⁸)R¹¹, said alkyl, cycloalkyl, aryl and heteroaryl groups optionally substituted with 1 or more substituents selected from hydroxy, halo, $C_1$ to $C_4$ perfluoroalkyl, $C_1$ to $C_4$ alkoxy, aryl, heteroaryl, guanidino, morpholino, tetrazol-5-yl, —COR⁸, —CO₂R⁸, —CONHSO₂R⁹, —CONR⁸R⁸, —O—COR⁸, —NR⁸R⁸, —NR¹²COOR⁹, —N($C_1$ to $C_6$ alkyl)piperazine, —SR⁹, —SOR⁹, —SO₂R⁹, —SO₂NR⁸CN, —SO₂NR⁸COR⁹, —SO₂NR⁸-heteroaryl, —PO(OR⁸)₂ and —PO(OR⁸)R¹³;

$L^1$ and $L^2$, $L^2$ and $L^3$, $L^3$ and $L^4$ or $L^4$ and $L^5$, when taken together with the azacyclic group to which they are attached, form a fused 8 to 11 member azabicyclic system having 1 to 5 nitrogen atoms and 0 to 3 atoms selected from oxygen and sulfur, said azabicyclic system optionally substituted with 1 to 3 $W^6$ substituents;

each $W^6$ substituent is independently halo, nitro, cyano, $C_1$ to $C_6$ alkyl, $C_3$ to $C_7$ cycloalkyl, polyfluoro-$C_1$ to $C_4$ alkyl, aryl, heteroaryl, tetrazol-5-yl, —COR⁸, —CO₂R⁸, —CONR⁸SO₂R⁹, —CONR⁹R¹⁰, —CONR⁸(tetrazol-5yl), —OR⁹, —OCONR⁹R¹¹, —NR⁸R⁹, —NR⁸COR⁹, —NR⁸CO₂R⁹, —NR⁸CONR⁸R⁹, —NR⁸SO₂R⁹, —NR⁸SO₂NR⁹R¹¹, —NR⁸SO₂-polyfluorophenyl, —SR⁹, —SOR⁹, —SO₂R⁹, —SO₂NR⁸CN, —SO₂NR⁹R¹², —SO₂NR⁸COR⁹, —SO₂NR⁸-heteroaryl, —PO(OR⁸)₂ or —PO(OR⁸)R¹¹, said alkyl, cycloalkyl, aryl and heteroaryl groups optionally substituted with 1 or more substituents selected from hydroxy, halo, $C_1$ to $C_4$ perfluoroalkyl, $C_1$ to $C_4$ alkoxy, aryl, heteroaryl, guanidino, morpholino, tetrazol-5-yl, —COR⁸, —CO₂R⁸, —CONR⁸SO₂R⁹, —CONR⁸R⁹, —O—COR⁸, —NR⁸R⁹, —NR¹²COOR⁹, —N($C_1$ to $C_6$ alkyl)piperazine, —SR⁹, —SOR⁹, —SO₂R⁹, —SO₂NR⁸CN, —SO₂NR⁸COR⁹, —SO₂NR⁸-heteroaryl, —PO(OR⁸)₂ and —PO(OR⁸)R¹³;

each $R^8$ is independently hydrogen, $C_1$ to $C_6$ alkyl, $C_3$ to $C_7$ cycloalkyl, aryl, heteroaryl or aryl($C_1$ to $C_6$)alkyl;

each $R^9$ is independently hydrogen, $C_1$ to $C_{10}$ alkyl, $C_3$ to $C_7$ cycloalkyl, aryl, heteroaryl or polyfluoro($C_1$ to $C_4$)alkyl, said alkyl and cycloalkyl optionally substituted with 1 or more substituents selected from halo, hydroxy, nitro, $C_1$ to $C_4$ alkoxy, $C_1$ to $C_4$ alkylthio, —CO₂R¹², amino, $C_1$ to $C_4$ alkylamino, di($C_1$ to $C_4$)alkylamino, aryl, heteroaryl, —SH, —PO₃H₂, —P(O)(OH)(O—$C_1$ to $C_4$ alkyl), P(O)(OR⁸)(R¹¹) or P(O)(OR¹⁴)(R¹⁵);

each $R^{10}$ is independently hydrogen, $C_1$ to $C_5$ alkyl, aryl or —$CH_2$-aryl;

each $R^{11}$ is independently hydrogen, $C_1$ to $C_5$ alkyl, $C_3$ to $C_7$ cycloalkyl, aryl or —$CH_2$-aryl;

each $R^{12}$ is hydrogen or $C_1$ to $C_4$ alkyl;

each $R^{13}$ is independently hydrogen, $C_1$ to $C_5$ alkyl, C2 to $C_4$ alkenyl, $C_1$ to $C_4$ alkoxy($C_1$ to $C_4$)alkyl or benzyl, said benzyl optionally substituted with 1 or more substituents independently selected from hydroxy, amino, nitro and methoxy;

$R^{14}$ and $R^{15}$ are taken together and form a 5 to 7 member ring having 1 to 3 atoms independently selected from nitrogen, oxygen and sulfur;

$M^1$ and $M^2$ are taken together and are —$(CH_2)_m$; and m is an integer from 3 to 7.

The preferred compounds are those of Formula I wherein: X is

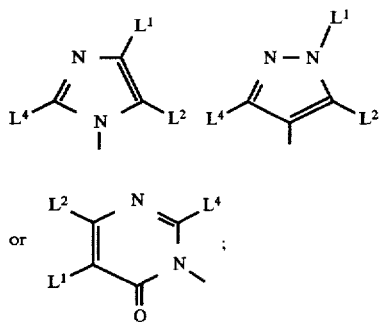

$L^1$, $L^2$ and $L^4$ are as defined above;

Q is thiophene, pyridine, pyrimidine, naphthyl, benzofuran or any of the foregoing substituted with 1 or 2 $W^1$ substituents;

$R^1$ and $R^2$ are taken together as defined above;

$R^3$ is —$(CH_2)_nCOR^4$;

n is 0 or 1;

$R^4$ is hydrogen, hydroxy or —OY;

Y is a pharmaceutically acceptable cation or a group hydrolyzable under physiological conditions; and each $W^1$ is independently halo, hydroxy, $C_1$ to $C_8$ alkyl, $C_3$ to $C_7$ cycloalkyl, $C_1$ to $C_7$ alkoxy, amino, $C_1$ to $C_7$ alkylamino, di($C_1$ to $C_7$ alkyl)amino, —CONRR or —COOR, wherein R is as defined above.

Particularly preferred are those compounds wherein X, Q, $R^3$, $R^4$, n and Y are as defined immediately above and wherein:

$R^1$ and $R^2$ are taken together and form a $C_5$ to $C_6$ carbocyclic, $C_8$ to $C_{10}$ carbobicyclic or 5 to 7 member heterocyclic group having 1 or 2 atoms independently selected from nitrogen, oxygen and sulfur, said carbocyclic, carbobicyclic or heterocyclic group being saturated, partially saturated or unsaturated;

$L^1$ and $L^2$, when taken separately, are each independently hydrogen, halo, $C_1$ to $C_6$ alkyl, $C_3$ to $C_7$ cycloalkyl, polyfluoro-$C_1$ to $C_4$ alkyl or —$CO_2R^8$;

$L^1$ and $L^2$, when taken together with the azacyclic group to which they are attached, form a fused 8 to 10 member azabicyclic system having 2 to 4 nitrogen atoms, said azabicyclic system optionally substituted with 1 to 3 $W^6$ substituents;

$L^4$ is $C_1$ to $C_4$ alkyl, $C_3$ to $C_5$ cycloalkyl or $C_1$ to $C_3$ alkoxy;

$R^8$ is hydrogen, $C_1$ to $C_6$ alkyl or $C_3$ to $C_7$ cycloalkyl; and each $W^6$ is independently halo, $C_1$ to $C_6$ alkyl, $C_3$ to $C_7$ cycloalkyl, polyfluoro-$C_1$ to $C_4$ alkyl, —$CO_2R^8$, amino, $C_1$ to $C_6$ alkylamino, di($C_1$ to $C_6$)alkylamino, acylamino or diacylamino.

Among the particularly preferred compounds defined above are those having the structure

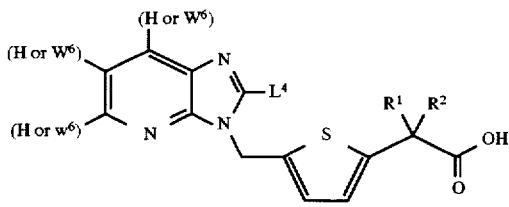

wherein:

$L^4$ is $C_1$ to $C_4$ alkyl or $C_3$ to $C_5$ cycloalkyl;

each $W^6$ is independently $C_1$ to $C_6$ alkyl, amino, $C_1$ to $C_6$ alkylamino, di($C_1$ to $C_6$)alkylamino, acylamino or diacylamino; and $R^1$ and $R^2$ are taken together and form cyclopentane, cyclohexane, cyclopentene, tetrahydropyran or indan, for example:

1-[5-(2-ethyl-5,7-dimethylimidazo[4,5-b]pyridin-3-ylmethyl)thiophen-2-yl]-cyclopent-3-ene carboxylic acid;

1-[5-(5,7-dimethyl-2-propylimidazo[4,5-b]pyridin-3-ylmethyl)thiophen-2-yl]cyclopent-3-ene carboxylic acid;

1-[5-(2-cyclopropyl-5,7-dimethylimidazo[4,5-b]pyridin-3-ylmethyl)thiophen-2-yl]cyclopent-3-ene carboxylic acid;

1-[5-(2-cyclopropyl-5,7-dimethylimidazo[4,5-b]pyridin-3-ylmethyl)thiophen-2-yl]cyclopentane carboxylic acid;

4-[5-(2-ethyl-5,7-dimethylimidazo[4,5-b]pyridin-3-ylmethyl)thiophen-2-yl]tetrahydropyran-4-carboxylic acid;

2-[5-(2-ethyl-5,7-dimethylimidazo[4,5-b]pyridin-3-ylmethyl)thiophen-2-yl]indan-2-carboxylic acid;

2-[5-(2-cyclopropyl-5,7-dimethylimidazo[4,5-b]pyridin-3-ylmethyl)thiophen-2-yl]indan-2-carboxylic acid;

1-[5-(2-ethyl-5,7-dimethylimidazo[4,5-b]pyridin-3-ylmethyl)thiophen-2-yl]cyclohexane carboxylic acid; and 1-[5-(2-cyclopropyl-5,7-dimethylimidazo[4,5-b]pyridin-3-ylmethyl)thiophen-2-yl]cyclohexane carboxylic acid.

Also among the particularly preferred compounds defined above are those having the structure

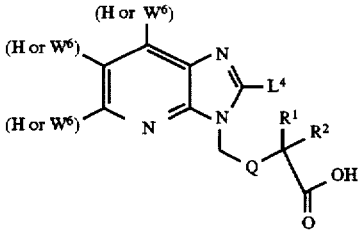

wherein:

Q is

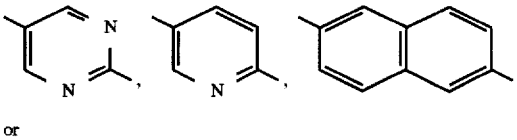

or

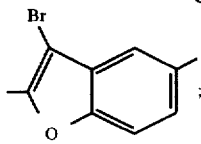

$L^4$ is $C_1$ to $C_4$ alkyl or $C_3$ to $C_5$ cycloalkyl; and $R^1$ and $R^2$ are taken together and are —$CH_2CH_2CH_2CH_2$— or —$CH_2CH=CHCH_2$—, for example:

1-|5-(2-ethyl-5,7-dimethylimidaz|4,5-b|pyridin-3-ylmethyl)pyridin-2-yl|cyclopentane carboxylic acid;

1-|5-(2-cyclopropyl-5,7-dimethylimidazo|4,5-b|pyridin-3-ylmethyl)pyridin-2-yl|cyclopentane carboxylic acid;

1-|2-(2-ethyl-5,7-dimethylimidazo|4,5-b|pyridin-3-ylmethyl)pyrimidin-5-yl|cyclopent-3-ene carboxylic acid;

1-|2-(2-cyclopropyl-5,7-dimethylimidazo|4,5-b|pyridin-3-ylmethyl)pyrimidin-5-yl|cyclopent-3-ene carboxylic acid;

1-|6-(2-ethyl-5,7-dimethylimidazo[4,5-b]pyridin-3-ylmethyl)naphthalen-2-yl|cyclopent-3-ene carboxylic acid; and 1-[3-bromo-5-(2-ethyl-5,7-dimethylimidazo|4,5-b|pyridin-3-ylmethyl)benzofuran-2-yl|cyclopentane carboxylic acid.

Also among the particularly preferred compounds defined above are those having the structure

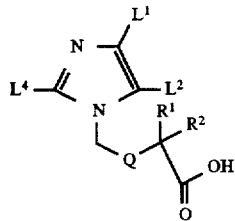

wherein:
Q is

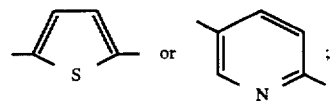

$L^1$ and $L^2$ are taken separately and are each independently halo, $C_1$ to $C_6$ alkyl or —$CO_2H$;

$L^4$ is $C_1$ to $C_4$ alkyl; and $R^1$ and $R^2$ are taken together and are —$CH_2CH_2CH_2CH_2$— or —$CH_2CH=CHCH_2$—, for example:

2-butyl-3-|5-(1-carboxycyclopent-3-enyl)thiophen-2-ylmethyl|-5-chloro-3H-imidazole-4-carboxylic acid;

3-|5-(1-carboxycyclopent-3-enyl)thiophen-2-ylmethyl|-5-ethyl-2-propyl-3H-imidazole-4-carboxylic acid; and 3-|5-(1-Carboxycyclopent-3-enyl)thiophen-2-ylmethyl|-5-chloro-2-propyl-3H-imidazole-4-carboxylic acid.

Also among the particularly preferred compounds defined above are those having the structure

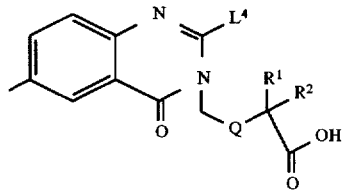

wherein:
Q is

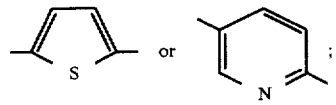

$L^4$ is $C_1$ to $C_4$ alkyl; and $R^1$ and $R^2$ are taken together and are —$CH_2CH_2CH_2CH_2$— or —$CH_2CH=CHCH_2$—, for example:

1-|5-(2-butyl-5-methyl-4-oxo-4H-quinazolin-3-ylmethyl)pyridin-2-yl|cyclopentane carboxylic acid; and 1-[5-(2-butyl-5-methyl-4-oxo-4H-quinazolin-3-ylmethyl)thiophen-2-yl|cyclopent-3-ene carboxylic acid.

Also among the particularly preferred compounds defined above are those having the structure

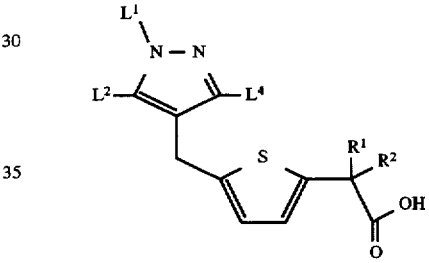

wherein:
$L^1$ and $L^2$ are taken separately and are each independently halo, $C_1$ to $C_6$ alkyl, polyfluoro-$C_1$ to $C_6$ alkyl or —$CO_2H$;

$L^4$ is $C_1$ to $C_4$ alkyl; and $R^1$ and $R^2$ are taken together and are —$CH_2CH_2CH_2CH_2$— or —$CH_2CH=CHCH_2$—, for example:

2,5-dibutyl-4-|5-(1-carboxycyclopent-3-enyl)thiophen-2-ylmethyl]-2H-pyrazole-3-carboxylic acid;

5-butyl-4-|5-(1-carboxycyclopent-3-enyl)thiophen-2-ylmethyl]-2-trifluoromethyl-2H-pyrazole-3-carboxylic acid; and 5-butyl-4-|5-(1-carboxycyclopent-3-enyl)thiophen-2-ylmethyl]-2-propyl-2H-pyrazole-3-carboxylic acid.

Other preferred compounds include compounds in the same general class as:

1-[5-(2-cyclopropyl-5,7-dimethylimidazo|4,5-b|pyridin-3-ylmethyl)thiophen-2-yl|cyclopenten-3-ene carboxylic acid benzenesulfonamide;

1-|5-(2-cyclopropyl-5,7-dimethylimidazo|4,5-b|pyridin-3-ylmethyl)thiophen-2-yl|cyclopenten-3-ene carboxylic acid p-toluenesulfonamide;

1-|5-(2-cyclopropyl-5,7-dimethylimidazo|4,5-b|pyridin-3-ylmethyl)thiophen-2-yl|cyclopenten-3-ene carboxylic acid methanesulfonamide; and 1-|5-(2-cyclopropyl-5,7-dimethylimidazo|4,5-b|pyridin-3-ylmethyl)thiophen-2-yl|cyclopenten-3-ene carboxylic acid trifluoromethanesulfonamide.

Various intermediates form subject matter of the present invention. particularly intermediates such as those described in the examples hereinbelow, for example, and their analogous alkyl and substituted alkyl esters:

1-thiophen-2-yl-cyclopent-3-ene carboxylic acid ethyl ester;
1-(5-formylthiophen-2-yl)cyclopent-3-ene carboxylic acid ethyl ester;
1-(5-chloromethylthiophen-2-yl)cyclopent-3-ene carboxylic acid ethyl ester; and
1-|5-(2-ethyl-5,7-dimethylimidazo|4,5-b|pyridin-3-ylmethyl)thiophen-2-yl|cyclopent-3-ene carboxylic acid ethyl ester.

This invention also concerns pharmaceutical compositions comprising said compounds and methods of making and using said compounds. This invention relates also to pharmaceutically acceptable compositions of these novel compounds in combination with other antihypertensive and cardiotonic agents, including beta blockers, diuretics, angiotensin converting enzyme inhibitors, calcium channel blockers, atrial natriuretic factor peptidase inhibitors, renin inhibitors and digitalis. This invention further relates to the use of these novel compounds in the treatment of central nervous system disorders such as, for example, cognitive dysfunction including Alzheimer's disease, amnesia and senile dementia, depression, anxiety and dysphoria. Furthermore, they may be used to treat glaucoma and diabetic complications such as diabetic renal disease.

DETAILED DESCRIPTION OF THE INVENTION

As used herein, the following definitions are used. "Halo" means radicals derived from the elements fluorine, chlorine, bromine and iodine.

"Alkyl" means straight or branched saturated hydrocarbon radicals, for example, methyl, ethyl, n-propyl, isopropyl, n-butyl, isobutyl and t-butyl.

"Alkenyl" means straight or branched unsaturated hydrocarbon radicals, for example, ethenyl, 1- or 2-propenyl, 2-methyl-1-propenyl and 1- or 2-butenyl.

"Cycloalkyl" means a saturated carbocyclic radical, for example, cyclopropyl, cyclobutyl, cyclopentyl and cyclohexyl.

"Polyfluoroalkyl" means an alkyl group substituted with two or more fluorines, including, for example, perfluoroalkyl.

"Polyfluorophenyl" means a phenyl group substituted with two or more fluorines.

The compounds of the present invention may be prepared according to the methods shown below. Reactions are performed in a solvent appropriate to the reagents and materials and consistent with the chemical transformation desired. The reagents employed in the reaction must be suitable for the functionality present. Optimal yields may require minor changes in the synthetic steps. The compounds are purified by conventional techniques such as chromatography (e.g. flash column chromatography, medium pressure liquid chromatography and high pressure liquid chromatography) and/or crystallization.

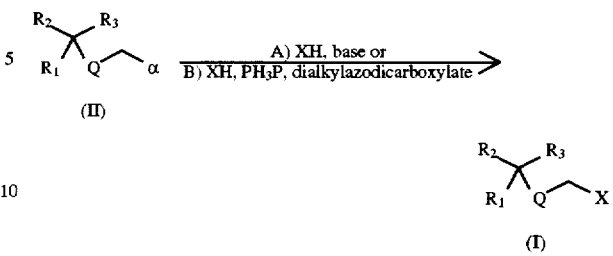

As shown in the General Reaction Scheme, above, the compounds of Formula I can be prepared by carrying out direct alkylation of alkali metal salts of azacyclics (XH, wherein X is an azacyclic group as defined above), using the appropriately protected heterocyclic, heterobicyclic or naphthyl methylene compounds of Formula II, above, wherein a is chloro, bromo, iodo, tosylate (OTS) or mesylate (OMS). The salts are prepared preferably using MH (wherein M is lithium, sodium or potassium) in a suitable solvent such as anhydrous dimethylformamide (DMF) or tetrahydrofuran (THF), or by treating XH with a metal alkoxide such as sodium or potassium methoxide, ethoxide or t-butoxide in an appropriate alcohol such as methanol, ethanol or t-butanol. The alkylation is generally carried out by dissolving the metal salt of the azacyclic in a solvent such DMF or dimethylsulfoxide (DMSO) and then treating it with the alkylating agent at between 20° C. and reflux temperature of the solvent for about 1 to about 24 hours. The alkylation step can in some cases produce a fully assembled compound of formula I except that functional groups in the alkylating agent II or in X may be present in protected form and require deprotection steps to be carried out to complete the synthesis.

In another variation of the General Reaction Scheme, above, compounds of Formula I can be prepared by reacting a compound of Formula II, wherein α is hydroxy, with the azacyclic (XH) in the presence of triphenylphosphine and dialkylazodicarboxylates, for example, di-t-butylazodicarboxylate.

The azacyclic (X) portion of the claimed compounds can be prepared as described immediately below, with the preparation of pyrazole-derived azacyclics shown in Scheme 5, below. The compounds of Formula II, above, can be prepared as shown in reaction Schemes 1 to 4 and 6.

Imidazoles of formula IIIa can be prepared by a variety of methods, for example, those described in EP 324377 and W092 00877. One of the preferred methods is shown below.

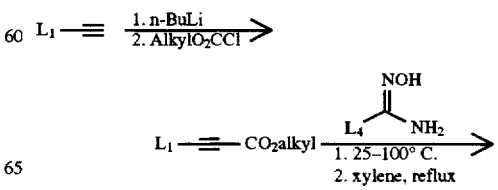

-continued

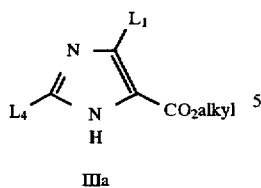

IIIa

An appropriately substituted acetylene is deprotonated with a base such as n-butyllithium (n-BuLi) in a polar solvent and is then treated with an alkyl halo carbonate. This compound can be treated with an appropriately substituted amidoxime having the structure

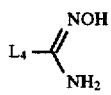

in a solvent such as diphenyl ether at temperatures ranging from about 100° to about 200° C., to afford IIIa after undergoing an intramolecular Cope rearrangement followed by an internal condensation.

Benzimidazoles of formula IIIb can be prepared by a variety of methods, for example, those described in EP 399731, EP 400977 and EP 420237. Two of the preferred methods are shown below.

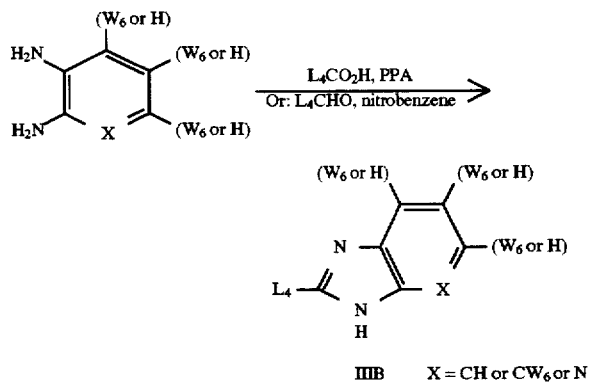

IIIB  X = CH or CW$_6$ or N

The vicinal heterocyclic diamines can be condensed with an appropriate carboxylic acid, nitrile, imidate ester or orthoester, either neat or in a solvent compatible with the starting materials and reagents such as polyphosphoric acid, ethanol, hydrocarbon solvents and with a catalytic amount of acid if required. Oxidation of an imine formed by reaction of diamine with an appropriate aldehyde using oxidants such as $Cu^{2+}$, nitrobenzene or DDQ also affords the desired azacyclics of formula IIIb.

Quinazolinones of formula IIIc can be prepared by a variety of methods, for example, those described in EP 407342, EP 411766, EP 481448 and EP 510812. One of the preferred methods is shown below.

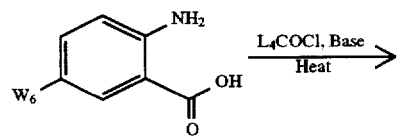

-continued

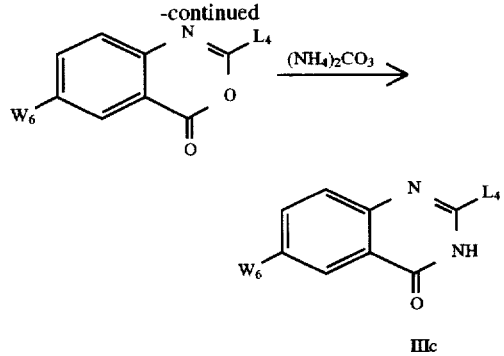

IIIc

A substituted anthranilic acid is treated with two equivalents of an acyl chloride in the presence of bases such as triethylamine and dimethylaminopyridine. The reaction product is then heated at temperatures ranging from about 50° to about 150° C. to give benzoxazones. Treatment with ammonium carbonate then affords the desired quinazolinone of formula IIIc.

The following reaction schemes outline methods for preparing the compounds of formula II, above, and are shown in detail in the examples.

SCHEME 1

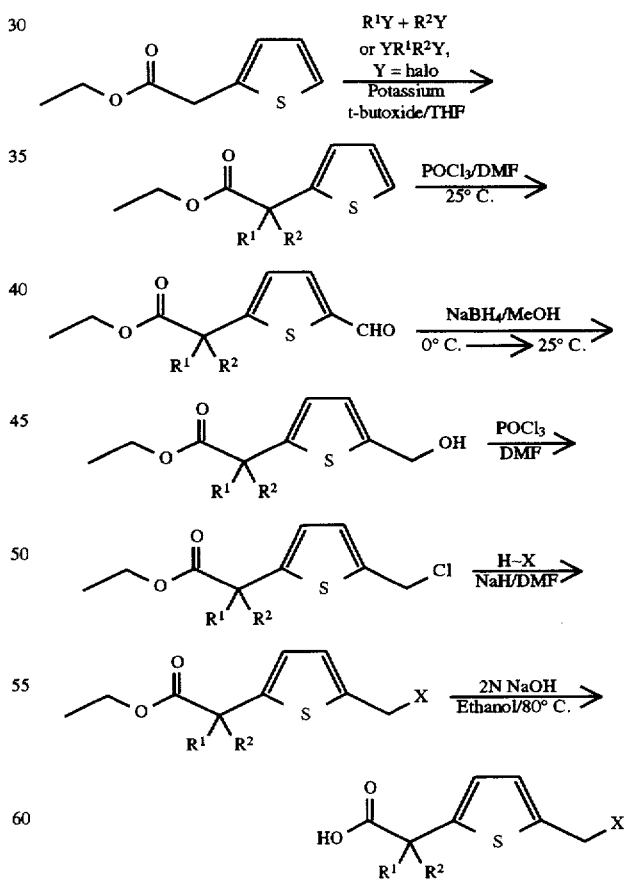

With regard to reaction scheme 1, above, the following chart summarizes how various compounds of the invention can be synthesized.

To synthesize:

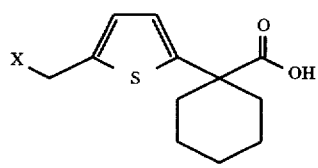
Use 1,5-Dichloropentane in Step 1 of Scheme 1

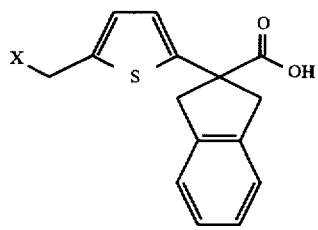
Use alpha, alpha-Dichloro-o-xylene in Step 1 of Scheme 1

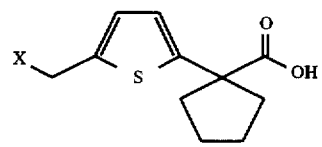
Use 1,4-Dichlorobutane in Step 1 of Scheme 1

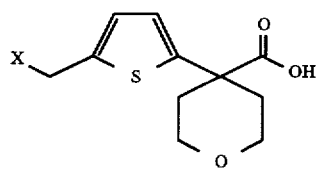
Use 1-Chloro-2-(2-chloro-ethoxy)-ethane in Step 1 of Scheme 1

SCHEME 2

n-Butyllithium/THF / Diethyl carbonate →

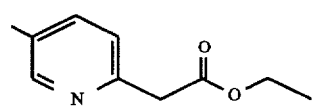
$R^1Y + R^2Y$ or $YR^1R^2Y$, Y = halo / Potassium t-butoxide →

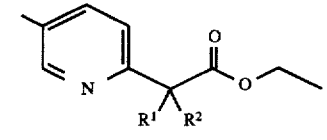
NBS/CCl₄ / AIBN →

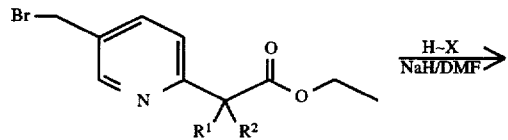
H–X / NaH/DMF →

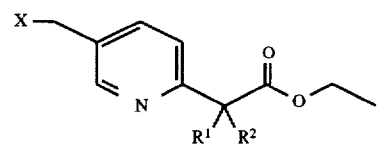
2N NaOH Methanol / 80° C. →

-continued
SCHEME 2

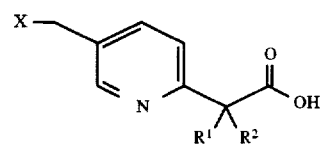

SCHEME 3

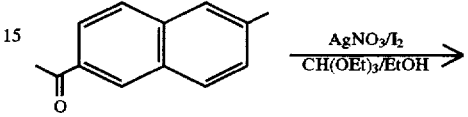
AgNO₃/I₂ / CH(OEt)₃/EtOH →

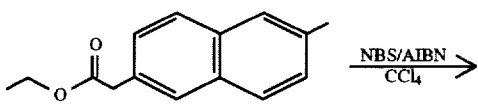
NBS/AIBN / CCl₄ →

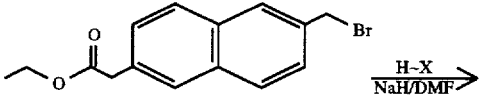
H–X / NaH/DMF →

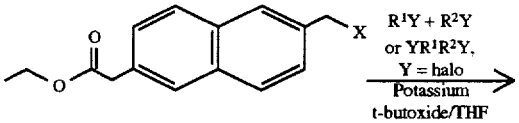
$R^1Y + R^2Y$ or $YR^1R^2Y$, Y = halo / Potassium t-butoxide/THF →

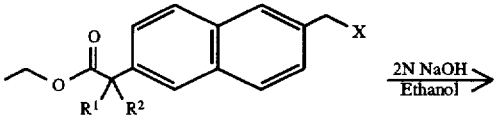
2N NaOH / Ethanol →

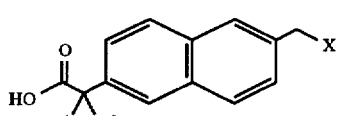

SCHEME 4

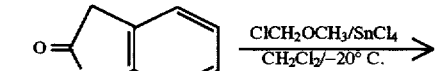
ClCH₂OCH₃/SnCl₄ / CH₂Cl₂/-20° C. →

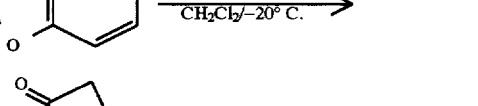
H₂/Pd/Carbon / EtOH/EtOAc/45psi →

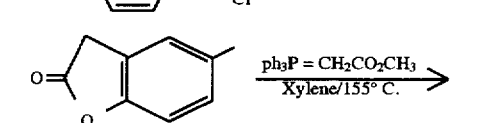
ph₃P=CHCO₂CH₃ / Xylene/155° C. →

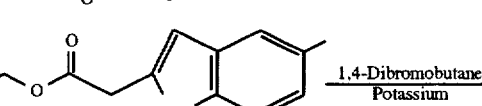
1,4-Dibromobutane / Potassium t-butoxide/THF →

SCHEME 4
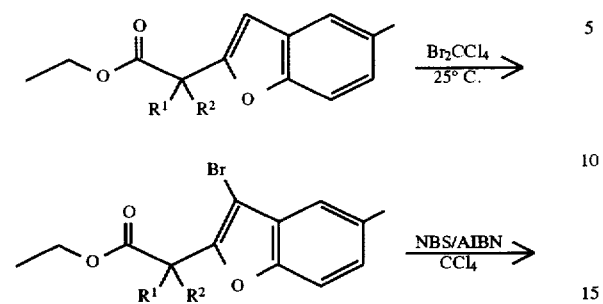
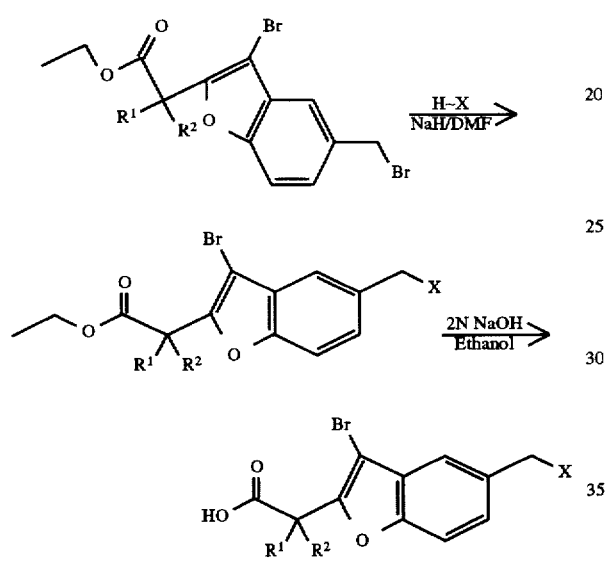
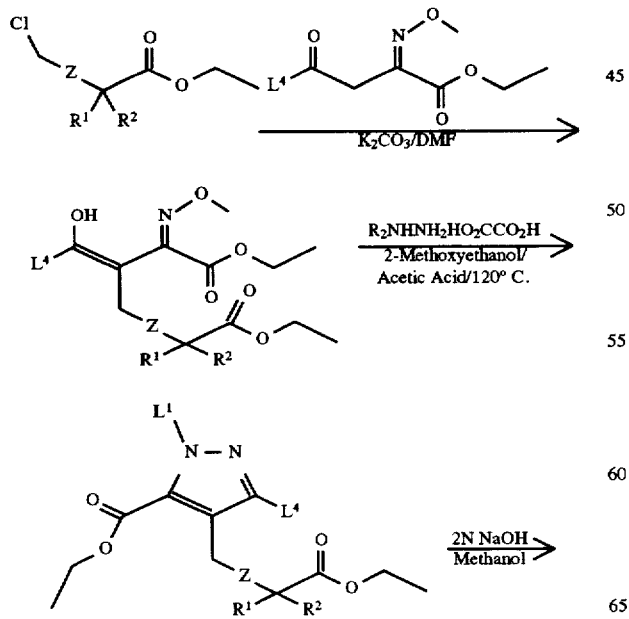
SCHEME 5
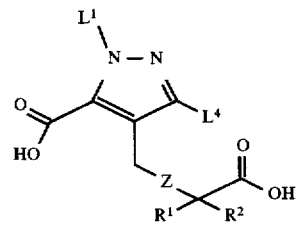
SCHEME 6
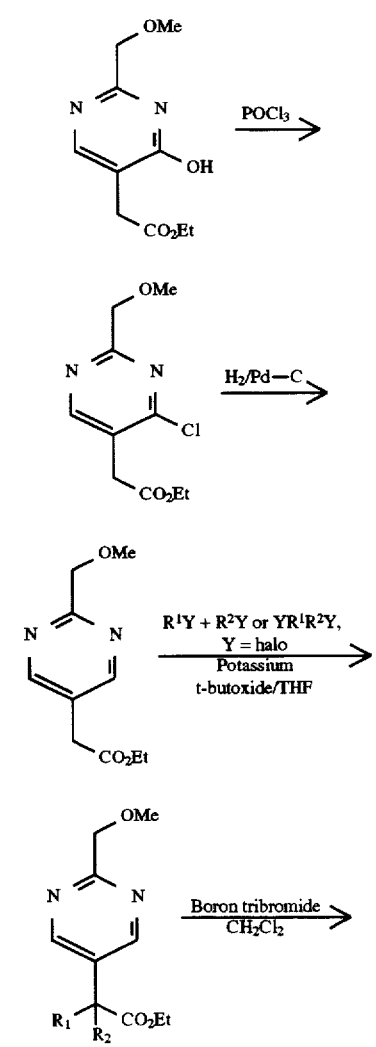

-continued
SCHEME 6

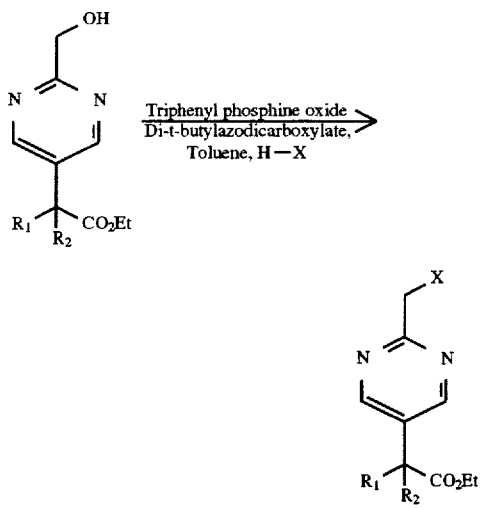

The compounds of the present invention are readily adapted to clinical use as modulators of AII action at the AII receptor. The ability of compounds of this invention to modulate AII action was determined by an in vitro AII rat liver binding assay which measures their ability to displace $^{125}$I sarcosine-1, isoleucine-8, angiotensin II (SARILE AII, obtained from New England Nuclear) from rat liver AII receptors. For this assay, the following materials are used.

Homogenation buffer (10 mM Tris, 0.2M sucrose, 1.0 mM EDTA), prepared using 1.21 g Tris base, 6.84 g sucrose and 336 mg EDTA in 1000 ml water, adjusted to pH 7.4 using HCl.

Buffer A (50 mM Tris, 5 mM MgCl$_2$), prepared using 6.05 g Tris base and 1.02 g MgCl$_2$.6H$_2$O in 1000 ml water.

Assay buffer, prepared using 200 ml Buffer A and 0.5 g BSA.

Male Sprague-Dawley rats are sacrificed by decapitation and the livers are removed quickly and placed in ice cold homogenation buffer (all the following procedures are performed at 4° C.). The liver is minced with scissors and homogenized in a chilled ground glass homogenizer at approximately 10 ml buffer/1 g liver (wet weight). The homogenate is centrifuged at 3000 g (5000 rpm, SM24 rotor) for 10 minutes, then the supernatant is centrifuged at 10,000 g for 13 minutes. The resulting supernatant is then centrifuged at 100,000 g for one hour. The pellet is resuspended in buffer A to an approximate concentration of 1 ml protein/ml. A BioRad protein assay using Coomassie blue dye is then run. The membrane preparation is aliquoted, frozen and stored at −20° C. On the day of the assay, the preparation is diluted with assay buffer to a final concentration of 600 µg/ml or with buffer A to a final concentration of 200 µg/ml. Due to the fact that some compounds of the invention bind to proteins, the use of BSA may interfere with some tests. Accordingly, the assay may be run with or without BSA; the differences are identified below.

The compound being tested is made up to an initial concentration of 2 mM in 100% DMSO. Dilutions are then made using 10% DMSO in assay buffer or buffer A. Radiolabelled (hot) SARILE AII is made up at 0.5 nM concentration in assay buffer or 1.0 nM concentration in buffer A. Non-radiolabelled (cold) SARILE AII is made up at 20 µM in 10% DMSO in assay buffer or buffer A for non-specific binding. Using microtitre plates, each incubate receives: 50 µl hot SARILE AII; 50 µl membrane preparation; and 100 µl buffer (total), cold SARILE AII (nonspecific binding) or compound to be tested. Each plate consists of the following in triplicate: total binding; nonspecific binding; and varying concentration of compound. Plates are incubated at room temperature for 40 minutes for assays containing BSA or for 120 minutes for assays without BSA, on a rocker plate at high speed. Plates are then aspirated using an Inotech cell harvester. The filters are cut, placed in test tubes and counted on a Gamma Counter. The mean for all triplicate points are calculated and total specific binding is calculated by subtracting nonspecific counts from total counts. Binding in the presence of compound (COUNTS) is calculated by subtracting nonspecific counts from counts in the presence of compound. Percent binding of SARILE AII in the presence of compound is calculated by dividing COUNTS by total specific counts. Percent inhibition is (1-percent binding) *100. IC$_{50}$ values (concentration of compound which inhibits binding by 50%) is read from a plot of percent inhibition (linear scale) versus compound concentration (log scale). Compounds of the present invention were found to have IC$_{50}$ values at or less than $10^{-5}$M.

The ability of compounds of the invention to lower blood pressure in mammals was determined by the following in vivo protocol. Sprague-Dawley rats are placed on a low sodium diet (Purina Labs, 0.07% sodium) for 15 days. On days 11 and 13 of this period, the rats are given furosemide (Lasix, 8 mg/kg, i.m.). On day 13, the animals are anesthetized with a pentobarbital-chloral hydrate mixture (30 mg/kg pentobarbital sodium and 10 mg/kg chloral hydrate, i.p.) and the carotid artery and jugular vein are cannulated using PE50 tubing (Clay-Adams). After a 24 hour recovery period, the animals are injected on day 14 with Lasix (10 mg/kg, i.m.) and are placed in plexiglass chambers for blood pressure recording. After dosing rats by either the oral or parenteral routes with the compound being tested, blood pressure is monitored for 5 hours and is displayed on a polygraph. When possible, blood pressure is also checked after 24 hours. According to this protocol, compounds of the invention are effective in lowering mean arterial pressure at oral dosages from about 0.1 mg/kg to about 300 mg/kg, and at parenteral dosages from about 0.01 mg/kg to about 100 mg/kg, often with a duration of action of greater than 24 hours.

Also within the scope of this invention are the pharmaceutically acceptable salts of the compounds of this invention. The pharmaceutically acceptable acid salts are those formed from acids which form non-toxic acid salts, for example, hydrochloride, hydrobromide, sulfate, bisulfate, phosphate, acid phosphate, acetate, citrate, fumarate, gluconate, lactate, maleate, succinate, tartrate, methanesulfonate, benzenesulfonate, toluenesulfonate and formate salts. Pharmaceutically acceptable cationic salts include those non-toxic salts based on alkali and alkaline earth metals, for example, sodium, lithium, potassium, calcium and magnesium, as well as non-toxic ammonium, quaternary ammonium and amine cations, for example, ammonium, tetramethyl-ammonium, methylamine, dimethylamine, trimethylamine, ethylamine, diethylamine and triethylamine.

Such salts are formed by methods well known to those skilled in the art. The pharmaceutically acceptable salts of the novel compounds of the present invention are readily prepared by contacting said compounds with a stoichiometric amount of, in the case of a non-toxic cation, an appropriate metal hydroxide, alkoxide or amine in either aqueous solution or a suitable organic solvent. In the case of non-toxic acid salt, an appropriate mineral or organic acid in either aqueous solution or a suitable organic solvent can be used. The salt may then be obtained by precipitation or by evaporation of the solvent.

For treatment of the various conditions described above, the compounds of the invention and their pharmaceutically acceptable salts can be administered to the patient either alone or, preferably, in combination with pharmaceutically acceptable carriers or diluents in a pharmaceutical composition, according to standard pharmaceutical practice. A compound can be administered via a variety of conventional routes of administration including orally, parenterally and by inhalation. When the compounds are administered orally, the dose range will generally be from about 0.1 to about 50 mg/kg/day, based on the body weight of the subject to be treated, preferably from about 1 to about 10 mg/kg/day in single or divided doses. If parenteral administration is desired, then an effective dose will generally be from about 0.01 to about 10 mg/kg/day. In some instances it may be necessary to use dosages outside these limits, since the dosage will necessarily vary according to the age, weight and response of the individual patient as well as the severity of the patient's symptoms and the potency of the particular compound being administered.

For oral administration, the compounds of the invention and their pharmaceutically acceptable salts can be administered, for example, in the form of tablets, powders, lozenges, syrups or capsules, or as an aqueous solution or suspension. In the case of tablets for oral use, carriers which are commonly used include lactose and corn starch. Lubricating agents, such as magnesium stearate, are commonly added. In the case of capsules, useful diluents are lactose and dried corn starch. When aqueous suspensions are required for oral use, the active ingredient is combined with emulsifying and suspending agents. If desired, certain sweetening and/or flavoring agents can be added.

For intramuscular, intraperitoneal, subcutaneous and intravenous use, a sterile injectable solution of the active ingredient is usually prepared, and the pH of the solution should be suitably adjusted and buffered. For intravenous use, the total concentration of solute should be controlled to make the preparation isotonic.

EXAMPLES

The present invention is illustrated by the following examples. Proton nuclear magnetic resonance ($^1$H NMR) spectra were measured at 250 MHz unless otherwise indicated and peak positions are expressed in parts per million (ppm) downfield from tetramethylsilane. The peak shapes are denoted as follows: s, singlet; d, doublet; t, triplet; q, quartet; m, multiplet; br, broad. $^1$H NMR spectra were recorded on a Bruker AC250 spectrometer. All reactions were performed under a nitrogen atmosphere. Anhydrous methylene chloride, toluene and DMF were purchased from the Aldrich Chemical Co. and were used as received. THF was distilled from Na/Benzophenone prior to use. Commercially available reagents were used as received unless otherwise noted. N-bromosuccinimide (NBS) was recrystallized from $H_2O$ and dried thoroughly under high vacuum prior to use. Thin layer chromatography was performed on E. Merck Kieselgel 60 F254 plates (0.25 mm) and flash chromatography was performed using EM Science Silica Gel 60. Chromatography solvent mixtures are reported as volume ratios.

Example 1

1-[5-(2-ethyl-5,7-dimethylimidazo[4,5-b]pyridin-3-ylmethyl)thiophen-2-yl]-cyclopent-3-ene carboxylic acid (8)

Step 1. 1-thiophen-2-yl-cyclopent-3-ene carboxylic acid ethyl ester (2)

To a solution of thiophen-2-yl acetic acid ethyl ester (1) (980 mg, 5.76 mmol) in 10 ml of THF at -20° C. was added a 1M solution of potassium t-butoxide in THF (5.76 ml, 5.76 mM) over 15 minutes. After 30 minutes at -20° C., cis-1, 4-dichlorobut-2-ene (0.610 ml, 5.76 mmol) was added dropwise and the reaction was warmed to room temperature. After 20 minutes the reaction was recooled to -20° C. and treated with potassium t-butoxide in THF (5.76 ml, 5.76 mM). The reaction was allowed to warm to room temperature, then was heated at 50° C. for 30 minutes and quenched with saturated ammonium chloride solution. The solvents were removed in vacuo and the residue taken up in EtOAc and washed with water. The organic layer was washed with saturated sodium chloride and dried over $MgSO_4$ to yield the title compound (2) (450 mg) after chromatography on silica gel using 5% EtOAc in hexanes as the eluant.

$^1$H-NMR (CDCl$_3$): 7.15 (d, 1H), 6.97 (t, 1H), 6.95 (d, 1H), 5.70 (s, 2H), 4.15 (q, 2H), 3.35 (d, 2H), 2.85 (d, 2H), 1.20 (t, 3H).

Step 2. 1-(5-formylthiophen-2-yl)cyclopent-3ene carboxylic acid ethyl ester (3)

POCl$_3$ (275 mg, 1.8 mmol) was added to 1 ml DMF at ambient temperature and stirred for 30 minutes. The product of Step 1, above (2) (208 mg, 0.93 mmol), was dissolved in 1 ml DMF, added to the reaction mixture and stirred for 1 hour at ambient temperature. The reaction mixture was heated to 105° C. for 3 hours, cooled to ambient temperature, quenched with saturated sodium acetate solution and extracted (2×10 ml, EtOAc). The organics were washed with brine and dried over MgSO$_4$, filtered and concentrated to yield the title compound (3).

$^1$H-NMR (CDCl$_3$): 9.85 (s, 1H), 7.55 (d, 1H), 7.05 (d, 1H), 5.75 (s, 2H), 4.15 (q, 2H), 3.40 (d, 2H), 2.85 (d, 2H), 1.25 (t, 3H).

Step 3. 1-(5-hydroxymethylthiophen-2-yl)-cyclopent-3ene carboxylic acid ethyl ester (4)

To a solution of the product of Step 2, above (3) (0.93 mmol), in 3 ml methanol at 0° C. was added sodium borohydride (2.0 mmol). The reaction was slowly allowed to warm to ambient temperature and was stirred for 2 hours. The reaction was quenched with saturated ammonium chloride and extracted (2×10 ml EtOAc). The organic extracts were combined and washed with saturated sodium bicarbonate and brine, dried with MgSO$_4$, filtered and concentrated to yield the title compound (4).

$^1$H-NMR (CDCl$_3$): 6.82 (d, 1H), 6.80 (d, 1H), 5.70 (s, 2H), 4.75 (s, 2H), 4.15 (q, 2H), 3.35 (d, 2H), 2.80 (d, 2H), 1.25 (t, 3H).

Step 4. 1-(5-chloromethylthiophen-2-yl)-cyclopent-3-ene carboxylic acid ethyl ester (5)

To a solution of the product of Step 3, above (4), in DMF was added POCl$_3$ (1.1 equiv.) over 5 minutes. The reaction mixture was stirred at ambient temperature for 16 hours and then the mixture was poured into a saturated aqueous sodium acetate solution and extracted 3 times with EtOAc. The combined extracts were dried over MgSO$_4$, filtered and concentrated to obtain the title compound (5).

$^1$H-NMR (CDCl$_3$): 6.90 (d, 1H), 6.75 (d, 1H), 5.70 (s, 2H), 4.75 (s, 2H), 4.15 (q, 2H), 3.35 (d, 2H), 2.80 (d, 2H), 1.20 (t, 3H).

Step 5. 1-[5-(2-ethyl-5,7-dimethylimidazo[4,5-b]pyridin-3-ylmethyl)-thiophen-2-yl]cyclopent-3ene carboxylic acid ethyl ester (6)

To a suspension of petroleum ether washed NaH (1.1 equiv.) in DMF was added 2-ethyl-5,7-dimethylimidazo[4, 5-b]pyridine (7) (1.1 equiv.). The reaction mixture was stirred for 15 minutes at ambient temperature and then the product of Step 4, above (5) (1 equiv.), dissolved in DMF, was cannulated into the mixture of the anion in DMF. The reaction mixture was stirred at ambient temperature for 17 hours and was then poured into saturated NaCl solution and extracted 2 times with EtOAc. The combined extracts were dried over $MgSO_4$, filtered and concentrated to dryness. The crude material was chromatographed on silica gel with a gradient elution from 50% EtOAc in hexanes to 60% EtOAc in hexanes to yield the title compound (6).

$^1$H-NMR ($CDCl_3$): 6.85 (s, 1H), 6.75 (d, 1H), 6.70 (d, 1H), 5.65 (s, 2H), 5.50 (s, 2H), 4.10 (q, 2H), 3.30 (d, 2H), 2.90 (q, 2H), 2.75 (d, 2H), 2.61 (s, 3H), 2.60 (s, 3H), 1.35 (t, 3H), 1.20 (t, 3H).

Step 6. 1-[5-(2-ethyl-5,7-dimethylimidazo[4,5-b]pyridin-3-ylmethyl)thiophen-2-yl]cyclopent-3-ene carboxylic acid (8)

To a solution of the product of Step 5, above (6), in methanol was added an excess of 2N NaOH. The reaction mixture was heated to 80° C. for 1 hour, cooled to room temperature and the solvent evaporated. Water was added to the residue and the solution was extracted 2 times with EtOAc. The aqueous layer was acidified with 10% HCl and the resultant white suspension was extracted 2 times with EtOAc. The organics were dried over $MgSO_4$, filtered and concentrated to a solid. The solid was crystallized from EtOAc to yield the title compound (8).

$^1$H-NMR ($CDCl_3$): 6.85 (s, 1H), 6.80 (d, 2H), 5.70 (s, 2H), 5.45 (s, 2H), 3.40 (d, 2H), 2.80 (q, 2H), 2.75 (d, 2H), 2.60 (s, 3H), 2.50 (s, 3H), 1.05 (t, 3H).

Example 2

1-[5-(5,7-dimethyl-2-propylimidazo[4,5-b]pyridin-3-ylmethyl)thiophen-2-yl]cyclopent-3-ene carboxylic acid (11)

Step 1. 1-[5-(5,7-dimethyl-2-propylimidazo[4,5-b]pyridin-3-ylmethyl)thiophen-2-yl]cyclopent-3-ene carboxylic acid ethyl ester (9)

Alkylation was performed on (5) as described in Example 1, Step 5, above, using 2-propyl-5,7-dimethylimidazo[4,5-b]pyridine (10) to yield the title compound (9).

$^1$H-NMR ($CDCl_3$): 6.85 (s, 1H), 6.75 (d, 1H), 6.70 (d, 1H), 5.65 (s, 2H), 5.50 (s, 2H), 4.10 (q, 2H), 2.85 (t, 2H), 2.75 (d, 2H), 2.60 (s, 6H), 1.80 (m, 2H), 120 (t, 3H), 1.00 (t, 3H).

Step 2. 1-[5-(5,7-dimethyl-2-propylimidazo[4,5-b]pyridin-3-ylmethyl)thiophen-2-yl]cyclopent-3-ene carboxvlic acid (11)

Hydrolysis was carried out on the product of Step 1, above (9), as described in Example 1, Step 6 to obtain the title compound (11).

$^1$H-NMR ($CDCl_3$): 7.05 (s, 1H), 6.87 (d, 1H), 6.85 (d, 1H), 5.70 (s, 2H), 5.65 (s, 2H), 3.30 (d, 2H), 2.95 (t, 2H), 2.75 (d, 2H), 2.62 (s, 3H), 2.60 (s, 3H), 180 (q, 2H), 1.00 (t, 3H).

Example 3

1-[5-(2-cyclopropyl-5,7-dimethylimidazo[4,5-b]pyridin-3-ylmethyl)thiophen-2-yl]cyclopent-3-ene carboxylic acid (14)

Step 1. 1-[5-(2-cyclopropyl-5,7-dimethylimidazo[4,5-b]pyridin-3-yl-methyl)thiophen-2-yl]cyclopent-3-ene carboxylic acid ethyl ester (12)

Alkylation was performed on (11) as described in Example 1, Step 5, using 2-cyclopropyl-5,7-dimethylimidazo[4,5-b]pyridine (13) to obtain the title compound (12).

$^1$H-NMR (250 MHz, $CDCl_3$): 6.85 (s, 1H), 6.80 (d, 1H), 6.74 (d, 1H), 5.68 (s, 2H), 5.60 (s, 2H), 4.04 (q, 2H), 3.28 (d, 2H, J=14.2 Hz), 2.75 (d, 2H, J=14 Hz), 2.60 (s, 3H), 2.56 (s, 3H), 2.02 (m, 1H), 1.22 (m, 5H), 1.05 (m, 2H).

Step 2. 1-[5-(2-cyclopropyl-5,7-dimethylimidazo[4,5-b]pyridin-3-ylmethyl)thiophen-2-yl]cyclopent-3-ene carboxylic acid (14)

Hydrolysis was carried out on the product of Step 1, above (12) as described in Example 1, Step 6 to yield the title compound (14), m.p. 184°–185° C.

$^1$H-NMR (MeOD-d4): 7.00 (s, 1H), 6.90 (d, 1H), 6.85 (d, 1H), 5.75 (s, 2H), 5.70 (s, 2H), 3.30 (d, 2H), 2.75 (d, 2H), 2.60 (s, 3H), 2.55 (s, 3H), 2.25 (m, 1H), 1.15 (m, 4H).

Example 4

1-[5-(2-cyclopropyl-5,7-dimethylimidazo[4,5-b]pyridin-3-ylmethyl)thiophen-2-yl]cyclohexane carboxylic acid (20)

Step 1. 1-thiophen-2-ylcyclohexane carboxylic acid ethyl ester (15)

The dialkylation of (1) was performed as described in Example 1, Step 1 using 1,5-dichloropentane to obtain the title compound (15).

$^1$H-NMR (300 MHz, $CDCl_3$): 7.2 (d, 1H), 6.95 (m, 2H), 4.06 (q, 2H), 2.5 (m, 2H), 1.60 (m, 8H), 1.20 (t, 3H).

Step 2. 1-(5-formylthiophen-2-yl)cyclohexane carboxylic acid ethyl ester (16)

The title compound (16) was prepared as described in Example 1, Step 2, using the product of Step 1, above (15) as the starting material.

$^1$H-NMR (250 MHz, $CDCl_3$): 9.85 (s, 1H), 7.63 (d, 1H), 7.07 (d, 1H), 4.15 (q, 2H), 2.5 (m, 2H), 1.5 (m, 8H), 1.20 (t, 3H).

Step 3. 1-(5-hydroxmethylthiophen-2-yl)-cyclohexane carboxylic acid ethyl ester (17)

The product of Step 2, above (16), was reduced as described in Example 1, Step 3 to yield the title compound (17).

$^1$H-NMR (250 MHz, $CDCl_3$): 6.85 (d, 1H, J=3.6 Hz), 6.80 (d, 1H), 4.75 (d, 2H, J=7.1 Hz), 4.15 (q, 2H), 2.5 (m, 2H), 1.5 (m, 8H), 1.25 (t, 3H).

Step 4. 1-(chloromethylthiophen-2-yl)cyclohexane carboxylic acid ethyl ester (18)

The product of Step 3, above (17), was chlorinated as described in Example 1, Step 4 to yield the title compound (18).

$^1$H-NMR (250 MHz , $CDCl_3$): 6.90 (d, 1H, J=3.5 H z) , 6.80 (d, 1H), 4.76 (s, 1H), 4.15 (q, 2H), 2.5 (m, 2H), 1.5 (m, 8H), 1.25 (t, 3H).

Step 5. 1-[5-(2-cyclopropyl-5,7-dimethylimidazo[4,5-b]pyridin-3-ylmethyl)thiophen-2-yl]cyclohexane carboxylic acid ethyl ester (19)

The product of Step 4, above (18), was alkylated as described in Example 1 Step 5, using 2-cyclopropyl-5,7-dimethylimidazo[4,5-b]pyridine (13) to yield the title compound (19).

$^1$H-NMR ($CDCl_3$): 6.85 (s, 1H), 6.82 (d, 1H), 6.70 (d, 1H), 5.60 (s, 2H), 4.10 (q, 2H), 2.60 (s, 3H), 2.55 (s, 3H), 2.40 (m, 2H), 2.00 (m, 2H), 1.50 (bm, 9H), 1.15 (t, 3H), 1.05 (m, 2H).

Step 6. 1-[5-(2-cyclopropyl-5,7-dimethylimidazo[4,5-b]pyridin-3-ylmethyl)thiophen-2-yl]cyclohexane carboxylic acid (20)

Hydrolysis was carried out on the product of Step 5, above (19) as described in Example 1, Step 6, to yield the title compound (20), m.p. 175°–176° C.

$^1$H-NMR (MeOD-d4): 7.00 (s, 1H), 6.95 (d, 1H), 6.85 (d, 1H), 5.75 (s, 2H), 2.65 (s, 3H), 2.60 (s, 3H), 2.40 (bm, 2H), 2.25 (m, 1 H), 1.60 (bm, 1 OH), 1.15 (m, 2H).

Example 5

1-[5-(2-ethyl-5,7-dimethylimidazo[4,5-b]pyridin-3-ylmethyl)thiophen-2-yl]cyclohexane carboxylic acid (22)

Step 1. 1-[5-(2-ethyl-5,7-dimethylimidazo[4,5-b]pyridin-3-ylmethyl)thiophen-2-yl]cyclohexane carboxylic acid ethyl ester (21)

The product of Example 4, Step 4, above (18), was alkylated as described in Example 1, Step 5, using 2-ethyl-5,7-dimethylimidazo[4,5-b]pyridine (7) to obtain the title compound (21).

$^1$H-NMR (CDCl$_3$): 6.85 (s, 1H), 6.75 (d, 1H), 6.70 (d, 2H), 5.50 (s, 2H), 4.10 (q, 2H), 2.90 (q, 2H), 2.60 (s, 6H), 2.40 (m, 2H), 1.60 (bm, 8H), 1.35 (t, 3H), 1.15 (t, 3H).

Step 2. 1-[5-(2-ethyl-5,7-dimethylimidazo[4,5-b]pyridin-3-ylmethyl)thiophen-2-yl]cyclohexane carboxylic acid (22)

Hydrolysis was performed on the product of Step 1, above (21), as described in Example 1, Step 6, to obtain the title compound (22).

$^1$H-NMR (MeOD-d4): 7.05 (s, 1H), 6.90 (d, 1H), 6.85 (d, 1H), 5.65 (s, 2H), 3.60 (q, 2H), 2.62 (s, 3H), 2.60 (s, 3H), 2.40 (m, 2H), 1.65 (m, 8H), 1.35 (t, 3H).

Example 6

2-[5-(2-ethyl-5,7-dimethylimidazo[4,5-b]pyridin-3-ylmethyl)thiophen-2-yl]indan-2-carboxylic acid (28)

Step 1. 2-thiophen-2-ylindan-2-carboxylic acid ethyl ester (23)

Thiophen-2-yl-acetic acid ethyl ester (1) was dialkylated as described in Example 1, Step 1 using a-a-dichlorooxylene to obtain the title compound (23).

$^1$H-NMR (300 MHz, CDCl$_3$): 7.25 (m, 2H), 7.17 (m, 2H), 7.0 (d, 1H), 6.93 (m, 2H), 4.15 (q, 2H), 3.94 (d, 2H, J=18 Hz), 3.42 (d, 2H, J=18 Hz), 1.20 (t, 3H).

Step 2. 2-(5-formylthiophen-2-yl)indan-2-carboxylic acid ethyl ester (24)

The title compound (24) was synthesized as described in Example 1, Step 2 using the product of Step 1, above (23) as the starting material.

$^1$H-NMR (250 MHz, CDCl$_3$): 9.81 (s, 1H), 7.60 (d, 1H, J=4 Hz), 7.20 (m, 4H), 7.10 (d, 1H, J=4 Hz), 4.16 (q, 2H), 3.94 (d, 2H, J=15 Hz), 3.45 (d, 2H, J=15 Hz), 1.25 (t, 3H).

Step 3. 2-(5-hydroxymethylthiophen-2-yl)-indan-2-carboxylic acid ethyl ester (25)

The product of Step 2, above (24) was reduced as described in Example 1, Step 3, to yield the title compound (25).

$^1$H-NMR (300 MHz, CDCl$_3$): 7.20 (m, 4H), 6.87 (d, 1H), 6.82 (d, 1H), 4.75 (d, 2H, J=6.8 Hz), 4.15 (q, 2H), 3.88 (d, 2H, J=15.4 Hz), 3.41 (d, 2H, J=15.4 Hz), 1.2 (t, 3H).

Step 4. 2-(5-chloromethylthiophen-2-yl)-indan-2-carboxylic acid ethyl ester (26)

The product of Step 3, above (25), was chlorinated as described in Example 1, Step 4 to obtain the title compound (26).

$^1$H-NMR (250 MHz, CDCl$_3$): 7.2 (m, 4H), 6.86 (d, 1H), 6.80 (d, 1H), 4.72 (s, 2H), 4.15 (q, 2H), 3.88 (d, 2H, J=15 Hz), 3.39 (d, 2H, J=15 Hz), 1.25 (t, 3H).

Step 5. 2-[5-(2-ethyl-5,7-dimethylimidazo[4,5-b]pyridin-3-ylmethyl)thiophen-2-yl]indan-2-carboxylic acid ethyl ester (27)

The product of Step 4, above (26), was alkylated as described in Example 1, Step 5 using 2-ethyl-5,7-dimethylimidazo[4,5-b]pyridine (7) to yield the title compound (27).

$^1$H-NMR (CDCl$_3$): 7.15 (m, 4H), 6.85 (s, 1H), 6.75 (m, 2H), 5.50 (s, 2H), 4.10 (q, 2H), 3.80 (d, 2H), 3.30 (d, 2H), 2.90 (q, 2H), 2.60 (s, 6H), 1.35 (t, 3H), 1.15 (t, 3H).

Step 6. 2-[5-(2-ethyl-5,7-dimethylimidazo[4,5-b]pyridin-3-ylmethyl)thiophen-2-yl]indan-2-carboxylic acid (28)

Hydrolysis was performed on the product of Step 5, above (27), as described in Example 1, Step 6, to yield the title compound (28), m.p. 243°–244° C.

$^1$H-NMR (MeOD-d4): 7.15 (bm, 4H), 7.05 (s, 1H), 6.85 (m, 2H), 5.65 (s, 2H), 3.80 (d, 2H), 3.30 (d, 2H), 2.95 (q, 2H), 2.65 (s, 6H), 1.30 (t, 3H).

Example 7

2-[5-(2-cyclopropyl-5,7-dimethylimidazo[4,5-b]pyridin-3-ylmethyl)thiophen-2-yl]indan-2-carboxylic acid (30)

Step 1. 2-[5-(2-cyclopropyl-5,7-dimethylimidazo[4,5-b]pyridin-3-ylmethyl)thiophen-2-yl]indan-2-carboxylic acid ethyl ester (29)

The product of Example 6, Step 4, above (26), was alkylated as described in Example 1, Step 5, using 2-cyclopropyl-5,7-dimethylimidazo[4,5-b]pyridine (13) to obtain the title compound (29).

$^1$H-NMR (CDCl$_3$): 7.15 (m, 4H), 6.85 (s, 1H), 6.75 (m, 2H), 5.50 (s, 2H), 4.10 (q, 2H), 3.80 (d, 2H), 3.35 (d, 2H), 2.60 (s, 3H), 2.50 (s, 3H), 2.00 (m, 1H), 1.17 (t, 3H), 1.15 (bm, 4H).

Step 2. 2-[5-(2-cyclopropyl-5,7-dimethylimidazo[4,5-b]pyridin-3-ylmethyl)thiophen-2-yl]indan-2-carboxylic acid (30)

Hydrolysis was carried out on the product of Step 1, above (29), as described in Example 1, Step 6, to yield the title compound (30), m.p. 250°–252° C.

$^1$H-NMR (MeOD-d4): 7.15 (bm, 4H), 7.00 (s, 1H), 6.90 (m, 2H), 5.75 (s, 2H), 3.80 (d, 2H), 3.30 (d, 2H), 2.62 (s, 3H), 2.58 (s, 3H), 2.20 (m, 1H), 1.15 (m, 4H).

Example 8

1-[5-(2-cyclopropyl-5,7-dimethylimidazo[4,5-b]pyridin-3-ylmethyl)thiophen-2-yl]cyclopentane carboxylic acid (36)

Step 1. 1-thiophen-2-ylcyclopentane carboxylic acid ethyl ester (31)

Thiophen-2-yl acetic acid ethyl ester (1) was dialkylated as described in Example 1, Step 1, using 1,4-dichlorobutane to obtain the title compound (31).

$^1$H-NMR (300 MHz, CDCl$_3$): 7.16 (d, 1H), 6.95 (m, 2H), 2.6 (m, 2H), 2.10 (m, 2H), 1.75 (m, 4H), 1.40 (t, 3H).

Step 2. 1-(5-formylthiophen-2-yl)cyclopentane carboxylic acid ethyl ester (32)

The title compound (32) was synthesized as described in Example 1, Step 2, using the product of Step 1, above (31), as the starting material.

$^1$H-NMR (300 MHz, CDCl$_3$): 9.82 (s, 1H), 7.6 (d, 1H), 7.05 (d, 1H), 4.12 (q, 2H), 2.58 (m, 2H), 2.05 (m, 2H), 1.75 (m, 4H), 1.2 (t, 3H).

Step 3. 1-(5-hydroxymethylthiophen-2-yl)-cyclopentane carboxylic acid ethyl ester (33)

The product of Step 2, above (32), was reduced as described in Example 1, Step 3 to yield the title compound (33).

$^1$H-NMR (250 MHz, CDCl$_3$): 6.84 (m, 2H), 4.77 (s, 2H), 4.12 (q, 2H), 2.55 (m, 2H), 2.06 (m, 2H), 1.75 (m, 4H), 1.2 (t, 3H).

Step 4. 1-(5-chloromethylthiophen-2-yl)-cyclopentane carboxylic acid ethyl ester (34)

The product of Step 3, above (33), was chlorinated as described in Example 1, Step 4 to yield the title compound (34).

¹H-NMR (300 MHz, CDCl₃): 6.92 (d, 1H), 6.78 (d, 1H), 4.78 (s, 2H), 4.10 (q, 2H), 2.5 (m, 2H), 2.05 (m, 2H), 1.75 (m, 4H), 1.20 (t, 3H).

Step 5. 1-[5-(2-cyclopropyl-5,7-dimethylimidazo[4,5-b]pyridin-3-ylmethyl)thiophen-2-yl]cyclopentane carboxylic acid ethyl ester (35)

The product of Step 4, above (34), was alkylated as described in Example 1, Step 5, using 2-cyclopropyl-5,7-dimethylimidazo[4,5-b]pyridine (1 3) to obtain the title compound (35).

¹H-NMR (CDCl₃): 6.85 (s, 1H), 6.80 (d, 1H), 6.70 (d, 1H), 5.60 (s, 2H), 4.10 (q, 2H), 2.60 (s, 3H), 2.55 (s, 3H), 2.50 (bm, 2H), 2.00 (bm, 3H), 1.65 (bm, 4H), 1.20 (bm, 2H), 1.17 (t, 3H), 1.05 (m, 2H).

Step 6. 1-[5-(2-cyclopropyl-5,7-dimethylimidazo[4,5-b]pyridin-3-ylmethyl)thiophen-2-yl]cyclopentane carboxylic acid (36)

Hydrolysis was carried out on the product of Step 5, above (35), as described in Example 1, Step 6, to yield the title compound (36).

¹H-NMR (MeOD-d4): 7.00 (s, 1H), 6.90 (d, 1H), 6.85 (d, 1H), 5.75 (s, 2H), 2.65 (s, 3H), 2.55 (s, 3H), 2.49 (m, 2H), 2.25 (m, 1H), 2.00 (m, 2H), 1.75 (m, 4H), 1.15 (m, 4H).

Example 9

4-[5-(2-ethyl-5,7-dimethylimidazo[4,5-b]pyridin-3-ylmethyl)thiophen-2-yl]tetrahydropyran-4-carboxylic acid (42)

Step 1. 4-thiophen-2-yltetrahydropyran-4-carboxylic acid ethyl ester (37)

Thiophen-2-yl-acetic acid ethyl ester (1) was dialkylated as described in Example 1, Step 1, using 1-chloro-2-(2-chloroethoxy)ethane to obtain the title compound (37).

¹H-NMR (250 MHz, CDCl₃): 7.2 (d, 1H), 6.95 (m, 2H), 4.2 (q, 2H), 3.88 (dt, 2H), 3.55 (dd, 2H), 2.5 (dt, 2H), 2.08 (dd, 1H), 1.25 (t, 3H).

Step 2. 4-(5-formylthiophen-2-yl)tetrahydropyran-4-carboxylic acid ethyl ester (38)

The title compound (38) was synthesized as described in Example 1, Step 2 using the product of Step 1, above (37), as the starting material.

¹H-NMR (250 MHz, CDCl₃): 9.88 (s, 1H), 7.67 (d, 1H), 7.10 (d, 1H), 4.21 (q, 2H), 3.9 (dt, 2H), 3.6 (dd, 2H), 2.54 (dt, 2H), 2.10 (dd, 1H), 2.06 (dd, 1H), 1.25 (t, 3H).

Step 3. 4-(5-hydroxymethylthiophen-2-yl)tetrahydropyran-4-carboxylic acid ethyl ester (39)

The product of Step 2, above (38), was reduced as described in Example 1, Step 3 to yield the title compound (39).

¹H-NMR (250 MHz, CDCl₃): 6.87 (d, 1H), 6.82 (d, 1H), 4.78 (s, 1H), 4.2 (q, 2H), 3.9 (dt, 2H), 3.48 (m, 2H), 2.48 (dt, 2H), 2.05 (m, 2H), 1.24 (t, 3H).

Step 4. 4-(5-chloromethylthiophen-2-yl)tetrahydropyran-4-carboxylic acid ethyl ester (40)

The product of Step 3, above (39), was chlorinated as described in Example 1, Step 4, to produce the title compound (40).

¹H-NMR (300 MHz, CDCl₃): 6.95 (d, 1H), 6.80 (d, 1H), 4.76 (s, 2H), 4.2 (q, 2H), 3.89 (dt, 2H), 3.58 (m, 2H), 2.5 (dt, 2H), 2.05 (m, 2H), 1.25 (t, 3H).

Step 5. 4-[5-(2-ethyl-5,7-dimethylimidazo[4,5-b]pyridin-3-ylmethyl)thiophen-2-yl]tetrahydropyran-4-carboxylic acid ethyl ester (41)

The product of Step 4, above (40), was alkylated as described in Example 1, Step 5, using 2-ethyl-5,7-dimethylimidazo[4,5-b]pyridine (7) to obtain the title compound (41).

¹H-NMR (CDCl₃): 6.90 (s, 1H), 6.80 (d, 1H), 6.70 (d, 1H), 5.50 (s, 2H), 4.15 (q, 2H), 3.80 (m, 2H), 3.50 (m, 2H), 2.90 (q, 2H), 2.60 (s, 6H), 2.40 (m, 2H), 2.00 (m, 2H), 1.35 (t, 3H), 1.20 (t, 3H).

Step 6. 4-[5-(2-ethyl-5,7-dimethylimidazo[4,5-b]pyridin-3-ylmethyl)thiophen-2-yl]tetrahydropyran-4-carboxylic acid (42)

Hydrolysis was performed on the product of Step 5, above (41), as described in Example 1, Step 6, to yield the title compound (42), m.p. 214°–215° C.

¹H-NMR (MeOD-d4): 6.90 (s, 1H), 6.85 (d, 1 H), 6.80 (d, 1 H), 5.50 (s, 2H), 3.85 (bt, 2H), 3.55 (t, 2H), 2.75 (q, 2H), 2.60 (s, 3H), 2.55 (s, 3H), 2.50 (bt, 2H), 2.05 (bt, 2H), 0.95 (t, 3H).

Example 10

1-[5-(2-ethyl-5,7-dimethylimidaz[4,5-b]pyridin-3-ylmethyl)pyridin-2-yl]cyclopentane carboxylic acid (47)

Step 1. (5-methylpyridin-2-yl)acetic acid ethyl ester (43)

To a solution of 2,5-lutidine (540 mg, 5.05 mM) in 10 ml of THF at –10° C. was added 2.5M n-butyllithium solution (2.0 ml, 5.00 mM). The resulting mixture was stirred for 30 minutes while allowing the temperature to rise to 0° C. The reaction was cooled to –50° C. and diethyl carbonate (0.61 ml, 5.00 mM) was added and the reaction was warmed to room temperature and stirred for 2 hours. The reaction was quenched with saturated NH₄Cl solution and extracted into EtOAc. The resulting organic layer was washed with saturated NaCl solution, dried over MgSO₄, filtered and concentrated to dryness. The residue was chromatographed on silica gel using 30% EtOAc/hexanes as the eluant to yield the title compound (43).

¹H-NMR (250 MHz, CDCl₃): 8.4 (s, 1H), 7.45 (d, 1H, J=6.4 Hz), 7.18 (d, 1H, J=6.4 Hz), 4.15 (q, 2H), 3.8 (s, 2H), 2.32 (s, 3H), 1.25 (t, 3H).

Step 2. 1-(5-methylpyridin-2-yl)cyclopentane carboxylic acid ethyl ester (44)

The product of Step 1, above (43), was dialkylated as described in Example 1, Step 1, using 1,4-dichlorobutane to obtain the title compound (44).

¹H-NMR (300 MHz, CDCl₃): 8.47 (s, 1H), 7.44 (d, 1H, J=6.8 Hz), 7.20 (d, 1H, J=6.8 Hz), 4.12 (q, 2H), 2.5 (m, 2H), 2.32 (s, 3H), 2.20 (m, 2H), 1.75 (m, 4H), 1.17 (t, 3H).

Step 3. 1-(5-bromomethylpyridin-2-yl)cyclopentanecarboxlic acid ethyl ester (45)

A mixture containing the product of Step 2, above (44) (1 equiv.), n-bromosuccinimide (1.1 equiv.), CCl₄ and a catalytic amount of azobisisobutyronitrile was heated at reflux for 4 hours, cooled to 0° C. and filtered through celite. The residue was washed well with CCl₄ and the filtrate was concentrated and chromatographed on silica gel to yield the title compound (45).

¹H-NMR (250 MHz, CDCl₃): 8.55 (d, 1H, J=1 Hz), 7.69 (dd, 1H, J=1, 7 Hz), 7.28 (d, 1H), 4.46 (s, 2H), 4.10 (q, 2H), 2.55 (m, 2H), 2.2 (m, 2H), 1.72 (m, 4H), 1.15 (t, 3H).

Step 4. 1-[5-(2-ethyl-5,7-dimethylimidaz[4,5-b]pyridin-3-yl-methyl)pyridin-2-yl]cyclopentane carboxylic acid ethyl ester (46)

The product of Step 3, above (45), was alkylated as described in Example 1, Step 5 using 2-ethyl-5,7-dimethylimidazo[4,5-b]pyridine (7) to yield the title compound (46).

¹H-NMR (CDCl₃): 8.50 (s, 1H), 7.40 (d, 1H), 7.20 (d, 1H), 6.90 (s, 1H), 5.40 (s, 2H), 4.10 (q, 2H), 2.85 (q, 2H), 2.60 (s, 3H), 2.55 (s, 3H), 2.45 (m, 2H), 2.15 (m, 2H), 1.70 (m, 4H), 1.35 (t, 3H), 1.15 (t, 3H).

27

Step 5. 1-|5-(2-ethyl-5,7-dimethylimidaz|4,5-b|pyridin-3-ylmethyl)pyridin-2-yl|cyclopentane carboxylic acid (47)

Hydrolysis was carried out on the product of Step 4, above (46), as described in Example 1, Step 6 to yield the title compound (47).

$^1$H-NMR (MeOD-d4): 8.35 (s, 1H), 7.50 (d, 1H), 7.25 (d, 1H), 7.00 (s, 1H), 5.55 (s, 2H), 2.90 (q, 2H), 2.60 (s, 3H), 2.55 (s, 3H), 2.05 (bm, 2H), 1.80 (bm, 2H), 1.70 (bm, 4H), 1.30 (t, 3H).

Example 11

1-|5-(2-cyclopropyl-5,7-dimethylimidazo|4,5-b|pyridin-3-ylmethyl)pyridin-2-yl|cyclopentane carboxylic acid (49)

Step 1. 1-|5-(2-cyclopropyl-5,7-dimethylimidazo|4,5-b|pyridin-3-ylmethyl)pyridin-2-yl|cyclopentane carboxylic acid ethyl ester (48)

The product of Example 10, Step 3, above (45), was alkylated as described in Example 1, Step 5, using 2-cyclopropyl-5,7-dimethylimidazo[4,5-b]pyridine (13) to produce the title compound (48).

$^1$H-NMR (CDCl$_3$): 8.55 (s, 1H), 7.50 (d, 1H), 7.20 (d, 1H), 6.85 (s, 1H), 5.55 (s, 2H), 4.10 (q, 2H), 2.55 (s, 3H), 2.52 (s, 3H), 2.50 (m, 2H), 2.15 (m, 2H), 1.19 (m, 1H), 1.70 (bm, 4H), 1.25 (m, 2H), 1.15 (t, 3H), 1.00 (m, 2H).

Step 2. 1-|5-(2-cyclopropyl-5,7-dimethylimidazo[4,5-b]pyridin-3-ylmethyl)pyridin-2-yl|cyclopentane carboxylic acid (49)

Hydrolysis was performed on the product of Step 1, above (48), as described in Example 1, Step 6 to yield the title compound (49).

$^1$H-NMR (MeOD-d4): 8.40 (s, 1H), 7.60 (d, 1H), 7.30 (d, 1H), 7.00 (s, 1H), 5.65 (s, 2H), 2.55 (s, 3H), 2.52 (s, 3H), 2.15 (m, 1H), 2.05 (bm, 2H), 1.85 (bm, 2H), 1.70 (bm, 4H), 1.10 (m, 4H).

Example 12

1-|6-(2-ethyl-5,7-dimethylimidazo[4,5-b]pyridin-3-ylmethyl)naphthalen-2-yl]cyclopent-3-ene carboxylic acid (54)

Step 1. (6-methylnaphthalen-2-yl)acetic acid ethyl ester (50)

Triethylorthoformate (1.5 ml) and 1-(6-methylnaphthalen-2-yl)ethanone (1.0 mmol) were dissolved in ethanol (4 ml). To the reaction mixture were added AgNO$_3$ (2.1 mmol) and I$_2$ (1.05 mmol) and the reaction mixture was heated to 80° C. for 20 hours. The reaction mixture was cooled to ambient temperature and concentrated to dryness. The residue was diluted eith EtOAc and filtered through celite. The combined organics were washed with saturated sodium bicarbonate solution and brine. The organic layer was then dried over MgSO$_4$, filtered and concentrated to dryness. The crude residue was chromatographed on silica gel using 5% EtOAc in hexanes as the eluant to yield the title compound (50).

$^1$H-NMR (CDCl$_3$): 7.74 (d, 1H), 7.72 (d, 1H), 7.70 (s, 1H), 7.60 (s, 1H), 7.35 (d, 1H), 7.30 (d, 1H), 4.15 (q, 2H), 3.75 (s, 2H), 2.50 (s, 3H), 1.25 (t, 3H).

Step 2. (6-bromomethylnaphthalen-2-yl)acetic acid ethyl ester (51)

To a solution of the product of Step 1, above (50) (3.07 mmol), in 6 ml of CCl$_4$ was added NBS (3.07 mmol) and azobisisobutyronitrile (0.09 mmol) and the mixture was heated to 82° C. for 2 hours. The reaction was cooled to ambient temperature and filtered through celite, washing the cake thoroughly with CCl$_4$. The organics were then concentrated to dryness to obtain the title compound (51).

28

$^1$H-NMR (CDCl$_3$): 7.81 (s, 1H), 7.80 (d, 1H), 7.75 (d, 1H), 7.70 (s, 1H), 7.50 (d, 1H), 7.45 (d, 1H), 4.65 (s, 2H), 4.15 (q, 2H), 3.75 (s, 2H), 1.25 (t, 3H).

Step 3. |6-(2-ethyl-5,7-dimethylimidazo|4,5-b|pyridin-3-ylmethyl)naphthalen-2-yl|acetic acid ethyl ester (52)

To a solution of 2-ethyl-5,7-dimethylimidazo|4,5-b| pyridine (7) (1.38 g, 6.5 mmol) in 4 ml DMF was added sodium hydride (250 mg, 6.5 mmol) and the reaction mixture was stirred 15 minutes at ambient temperature. The product of Step 2, above (51) (3.07 mmol), was dissolved in 3 ml DMF and added to the reaction mixture and stirred at ambient temperature for 16 hours. The reaction mixture was diluted with EtOAc and washed with saturated sodium bicarbonate solution and brine. The combined organics were then dried over MgSO$_4$, filtered and concentrated to dryness. The crude material was then chromatographed on silica gel using 50% EtOAc in hexanes as the eluant to yield the title compound (52) (95 mg).

$^1$H-NMR (CDCl$_3$): 7.72 (d, 1H), 7.70 (s, 1H), 7.65 (d, 1H), 7.45 (s, 1H), 7.40 (d, 1H), 7.28 (d, 1H), 6.90 (s, 1H), 4.15 (q, 2H), 3.75 (s, 2h), 2.80 (q, 2H), 2.65 (s, 3H), 2.60 (s, 3H), 1.28 (t, 3H), 1.25 (t, 3H).

Step 4. 1-|6-(2-ethyl-5,7-dimethylimidazo[4,5-b|pyridin-3-ylmethyl)naphthalen-2-yl]cyclopent-3-ene carboxylic acid ethyl ester (53)

To a solution of the product of Step 3, above (52) (95 mg, 0.24 mmol), in THF/DMPU (1 ml/0.25 ml) at −78° C., was added 1.0M solution of potassium t-butoxide in THF (0.24 ml, 0.24 mmol). The solution was stirred for 15 minutes at −78° C. and cis-1,4-dichlorobut-2-ene (0.025 ml, 0.24 mmol) was added. The reaction mixture was stirred at −78° C. for 10 minutes and a second equivalent of 1.0M potassium t-butoxide solution was added. The reaction mixture was warmed to −50° C. for 15 minutes, the cooling bath was removed and the mixture was stirred at ambient temperature for 15 minutes. The reaction was then heated to 80° C. for 2 hours. The reaction was cooled to ambient temperature, quenched with concentrated acetic acid, diluted with EtOAc and extracted from brine. The combined organics were then dried over MgSO$_4$, filtered and concentrated to dryness. The crude material was then chromatographed on silica gel using 50% EtOAc in hexanes as the eluant to yield the title compound (53) (35 mg).

$^1$H-NMR (CDCl$_3$): 7.72 (d, 1H), 1.15 (t, 3H), 7.68 (d, 1H), 7.65 (s, 1H), 7.49 (s, 1H), 7.45 (d, 1H), 7.25 (d, 1H), 6.90 (s, 1H), 5.80 (s, 2H), 5.60 (s, 2H), 4.10 (q, 2H), 3.45 (d, 2H), 2.85 (d, 2H), 2.65 (s, 3H), 2.60 (s, 3H), 2.25 (q, 2H), 1.30 (t, 3H).

Step 5. 1-|6-(2-ethyl-5,7-dimethylimidazo[4,5-b]pyridin-3-ylmethyl)naphthalen-2-yl]cyclopent-3-ene carboxylic acid (54)

A solution of the product of Step 4, above (53) (35mg), 2N NaOH (0.5 ml) and 2 ml of ethanol was heated at 80° C. for 20 hours. The reaction mixture was cooled to ambient temperature and the solvent was evaporated. The residue was dissolved in water and extracted (1×5 ml EtOAc). The aqueous solution was then neutralized with concentrated acetic acid and extracted (2×5 ml CHCl$_3$). The combined organics were dried over MgSO$_4$, filtered and concentrated to dryness. The residue was azeotroped with heptane to remove trace amounts of acetic acid. The crude material was diluted with EtOAc and hexanes were added to crash out the product, which was filtered and dried to yield the title compound (54).

$^1$H-NMR (DMSO-d6): 7.90 (d, 1H), 7.80 (d, 1H), 7.75 (s, 1H), 7.55 (s, 1H), 7.40 (d, 1H), 7.25 (d, 1H), 6.95 (s, 1H), 5.80 (d, 2H), 5.60 (s, 2H), 3.25 (d, 2H), 2.80 (q, 2H), 2.70 (d, 2H), 2.50 (s, 6H), 1.20 (t, 3H).

Example 13

1-[3-bromo-5-(2-ethyl-5,7-dimethylimidazo[4,5-b]pyridin-3-ylmethyl)benzofuran-2-yl]cyclopentane carboxylic acid (62)

Step 1. 5-chloromethyl-3H-benzofuran-2-one (55)

To a solution of 3H-benzofuran-2-one (7.45 mmol) and chlormethyl methyl ether (9.31 mmol) in 15 ml of $CH_2Cl_2$ at 0° C. was slowly added $SnCl_4$ (15 mmol). The reaction was slowly allowed to warm to ambient temperature and was stirred for 2 hours. The reaction was cooled to 0° C. and carefully quenched with saturated sodium bicarbonate. The mixture was extracted (2×EtOAc) and the organics were washed with brine. The combined organics were then dried over $MgSO_4$, filtered and concentrated to dryness. The crude residue was chromatographed on silica gel using 20% EtOAc in hexanes as the eluant to obtain the title compound (55).

$^1$H-NMR ($CDCl_3$): 7.83 (s, 1H), 7.80 (d, 1H), 7.10 (d, 1H), 4.60 (s, 2H), 3.75 (s, 2H).

Step 2. 5-methyl-3H-benzofuran-2-one (56)

A solution of the product of Step 1, above (55) (10.89 mmol), in ethanol/ethyl acetate (23 ml/5 ml) was added to 10 ml ethanol over 10% palladium catalyst on carbon (100 mg). The mixture was hydrogenated on a Parr shaker at 45 psi for 2 hours. The reaction mixture was filtered through celite and the organics were concentrated to dryness to obtain the title compound (56).

$^1$H-NMR ($CDCl_3$): 7.30 (d, 1H), 7.25 (s, 1H), 7.15 (d, 1H), 3.95 (s, 2H), 2.60 (s, 3H).

Step 3. (5-methylbenzofuran-2-yl)acetic acid ethyl ester (57)

A mixture of the product of Step 2, above (56) (10.81 mmol) and (carbethoxymethyl)triphenylphosphonium bromide (12.0 mmol) in 50 ml of xylene was heated to 155° C. for 20 hours. The reaction was cooled to ambient temperature and concentrated to dryness. The crude residue was chromatographed on silica gel with gradient elution with 5% EtOAc in hexanes to 10% EtOAc in hexanes to obtain the title compound (57).

$^1$H-NMR ($CDCl_3$): 7.37 (d, 1H), 7.35 (s, 1H), 7.10 (d, 1H), 6.55 (s, 1H), 4.20 (q, 2H), 3.90 (s, 2H), 2.45 (s, 3H), 1.30 (t, 3H).

Step 4. 1-(5-methylbenzofuran-2-yl)cyclopentane carboxylic acid ethyl ester (58)

To a solution of the product of Step 3, above (57) (1.85 mmol), in 2 ml DMF was added 60% sodium hydride in oil (3.6 mmol) at ambient temperature. The reaction mixture was stirred for 15 minutes and then 1,4-dibromobutane (1.85 mmol) was added. The reaction mixture was heated to 80° C. for 2 hours, cooled to ambient temperature, diluted with EtOAc and washed with saturated sodium bicarbonate and brine. The combined organics were then dried over $MgSO_4$, filtered and concentrated to dryness. The crude material was chromatographed on silica gel using 10% EtOAc in hexanes as the eluant to obtain the title compound (58).

Step 5. 1-(3-bromo-5-methylbenzofuran-2-yl)-cyclopentane carboxylic acid ethyl ester (59)

To a solution of product of Step 4, above (58) (1.0 mmol) in 2 ml $CCl_4$ was added bromine (1.0 mmol) at ambient temperature and the reaction mixture was stirred for 2 hours, refluxed for 1 hour to ensure completion of the reaction, cooled to ambient temperature, diluted with $CH_2Cl_2$ and washed with saturated sodium bicarbonate and brine. The combined organics were dried over $MgSO_4$, filtered and concentrated to dryness. The crude residue was chromatographed on silica gel using 5% EtOAc in hexanes as the eluant to obtain the title compound (59).

$^1$H-NMR ($CDCl_3$): 7.25 (d, 1H), 7.20 (s, 1H), 7.05 (d, 1H), 4.10 (q, 2H), 2.42 (m, 4H), 2.40 (s, 3H), 1.17 (m, 4H), 1.15 (t, 3H).

Step 6. 1-(3-bromo-5-bromomethylbenzofuran-2-yl)-cyclopentane carboxylic acid ethyl ester (60)

The product of Step 5, above (59), was brominated as described in Example 12, Step 2 to obtain the title compound (60).

$^1$H-NMR ($CDCl_3$): 7.50 (d, 1H), 7.40 (s, 1H), 7.35 (d, 1H), 4.15 (q, 2H), 2.45 (m, 4H), 1.75 (m, 4H), 1.20 (t, 3H).

Step 7. 1-[3-bromo-5-(2-ethyl-5,7-dimethylimidazo[4, 5-b]pyridin-3-ylmethyl)benzofuran-2-yl]cyclopentane carboxylic acid ethyl ester (61)

The product of Step 6, above (60), was alkylated as described in Example 12, Step 3 using 2-ethyl-5,7-dimethylimidazo[4,5-b]pyridine (7) to obtain the title compound (61).

$^1$H-NMR ($CDCl_3$): 7.35 (d, 1H), 7.30 (s, 1H), 7.05 (d, 1H), 6.90 (s, 1H), 5.55 (s, 2H), 4.15 (q, 2H), 2.80 (q, 2H), 2.65 (s, 3H), 2.60 (s, 3H), 2.45 (m, 4H), 1.75 (m, 4H), 1.35 (t, 3H), 1.20 (t, 3H).

Step 8. 1-[3-bromo-5-(2-ethyl-5,7-dimethylimidazo[4,5-b]pyridin-3-ylmethyl)benzofuran-2-yl]cyclopentane carboxylic acid (62)

Hydrolysis was carried out on the product of Step 7, above (61) as described in Example 12, Step 5 to yield the title compound (62).

$^1$H-NMR (MeOD-4): 7.40 (d, 1H), 7.25 (s, 1H), 7.15 (d, 1H), 7.05 (s, 1H), 5.65 (s, 2H), 2.85 (q, 2H), 2.62 (s, 3H), 2.58 (s, 3H), 2.45 (m, 4H), 1.70 (m, 4H), 1.25 (t, 3H).

Example 14

2-butyl-3-[5-(1-carboxycyclopent-3-enyl)thiophen-2-ylmethyl]-5-chloro-3H-imidazole-4-carboxylic acid (72)

Step 1. 2-butyl-5-chloro-3-[5-(1-ethoxycarbonylcyclopent-3-enyl)thiophen-2-ylmethyl]-3H-imidazole-4-carboxylic acid ethyl ester (71)

Alkylation was carried out on 1-(5-chloromethylthiophen-2-yl)cyclopent-3-ene carboxylic acid ethyl ester (5) as described in Example 1, Step 5, using 2-butyl-5-chloro-3H-imidazole-4-carboxylic acid ethyl ester (69) to yield the title compound (71).

$^1$H-NMR ($CDCl_3$): 6.73 (d, 1H), 6.72 (d, 1H), 5.70 (s, 2H), 5.60 (s, 2H), 4.35 (q, 2H), 4.15 (q, 2H), 3.30 (d, 2H), 2.75 (d, 2H), 2.70 (t, 2H), 1.70 (m, 2H), 1.40 (m, 2H), 1.35 (t, 3H), 0.95 (t, 3H).

Step 2. 2-butyl-3-[5-(1-carboxycyclopent-3-enyl)thiophen-2-ylmethyl]-5-chloro-3H-imidazole-4-carboxylic acid (72)

To a solution of the product of Step 1, above (71) (50 mg) in 2 ml of methanol was added 1 ml 2N NaOH. This mixture was stirred at ambient temperature for 2 hours, the solvent was removed and the residue taken up in water and extracted (2×EtOAc). The aqueous layer was then acidified with 10% HCl and extracted (3×EtOAc). The combined organics were dried over $MgSO_4$, filtered and concentrated to dryness to yield the title compound (72).

$^1$H-NMR ($CDCl_3$): 6.80 (d, 1H), 6.70 (d, 1H), 5.70 (s, 2H), 5.55 (s, 2H), 3.30 (d, 2H), 2.75 (t, 2H), 2.70 (t, 2H), 1.70 (m, 2H), 1.35 (m, 2H), 0.85 (t, 3H).

Example 15

3-[5-(1-carboxycyclopent-3-enyl)thiophen-2-ylmethyl]-5-ethyl-2-propyl-3H-imidazole-4-carboxylic acid (75)

Step 1. 3-[5-(1-ethoxycarbonylcyclopent-3-enyl)thiophen-2-ylmethyl]-5-ethyl-2-propyl-3H-imidazole-4-carboxylic acid ethyl ester (73)

Alkylation was carried out on 1-(5-chloromethylthiophen-2-yl)cyclopent-3-ene carboxylic acid ethyl ester (5) as described in Example 1, Step 5, using 5-ethyl-2-propyl-3H-imidazole-4-carboxylic acid ethyl ester (74) to obtain the title compound (73).

¹H-NMR (CDCl₃): 6.75 (d, 1H), 6.55 (d, 2H), 5.70 (s, 2H), 5.10 (s, 2H), 4.35 (q, 2H), 4.15 (q, 2H), 3.30 (d, 2H), 2.95 (q, 2H), 2.80 (d, 2H), 2.65 (t, 2H), 1.75 (m, 2H), 1.35 (t, 3H), 1.20 (t, 3H), 1.10 (t, 3H), 0.95 (t, 3H).

Step 2. 3-[5-(1-carboxycyclopent-3-enyl)thiophen-2-ylmethyl]-5-ethyl-2-propyl-3H-imidazole-4-carboxylic acid (75)

Hydrolysis was performed on the product of Step 1, above (73), as described in Example 14, Step 2, to yield the title compound (75), m.p. 157°–161° C.

¹H-NMR (MeOD-d4): 6.85 (d, 2H), 6.70 (d, 2H), 5.70 (s, 2H), 5.30 (s, 2H), 3.40 (d, 2H), 2.95 (q, 2H), 2.75 (t, 2H), 2.65 (t, 2H), 1.65 (m, 2H), 1.10 (t, 3H), 0.95 (t, 3H).

Example 16

3-[5-(1-Carboxycyclopent-3-enyl)thiophen-2-ylmethyl]-5-chloro-2-propyl-3H-imidazole-4-carboxylic acid (81)

Step 1. 1-[5-(4-chloro-5-formyl-2-propylimidazo-1-ylmethyl)thiophen-2-yl]cyclopent-3-ene carboxylic acid ethyl ester (78)

Alkylation was carried out on 1-(5-chloromethylthiophen-2-yl)cyclopent-3-ene carboxylic acid ethyl ester (5) as described in Example 1, Step 5, using 5-chloro-2-propyl-3H-imidazole-4-carbaldehyde (79) to produce the title compound (78).

¹H-NMR (CDCl₃): 9.75 (s, 1H), 6.80 (d, 1H), 6.75 (d, 1H), 5.70 (s, 2H), 5.60 (s, 2H), 4.15 (q, 2H), 3.30 (d, 2H), 2.75 (d, 2H), 2.70 (t, 2H), 1.75 (m, 2H), 1.20 (t, 3H), 1.00 (t, 3H).

Step 2. 5-chloro-3-[5-(1-ethoxycarbonylcyclopent-3-enyl)thiophen-2-ylmethyl]-2-propyl-3H-imidazole-4-carboxylic acid (80)

A solution of sodium chlorite (976 mg) and sodium dihydrogen phosphate (976 mg) in 5.0 ml water was added to a solution of the product of Step 1, above (78) (500 mg), 2-methyl-2-butene (893 mg) and t-butanol (12 ml) in 9.0 ml of THF at room temperature and was stirred for 1 hour. The solvent was removed from the reaction mixture and the residue extracted into EtOAc from water. The organic layer was dried over MgSO₄, filtered, evaporated to dryness and chromatographed on silica gel using 100% EtOAc to 20% MeOH in EtOAc as the gradient eluant to yield the title compound (80), m.p. 114°–115° C.

¹H-NMR (CDCl₃): 6.75 (s, 2H), 5.70 (s, 2H), 5.60 (s, 2H), 4.15 (q, 2H), 3.30 (d, 2H), 2.75 (d, 2H), 2.72 (t, 2H), 1.80 (m, 2H), 1.20 (t, 3H), 1.00 (t, 3H).

Step 3. 3-[5-(1-carboxycyclopent-3-enyl)thiophen-2-ylmethyl]-5-chloro-2-propyl-3H-imidazole-4-carboxylic acid (81)

Hydrolysis was performed on the product of Step 2, above (80), as described in Example 14, Step 2 to obtain the title compound (81), m.p. 170°–172° C.

¹H-NMR (MeOD-d4): 6.85 (s, 2H), 5.75 (s, 2H), 5.70 (s, 2H), 3.30 (d, 2H), 2.80 (m, 4H), 1.70 (m, 2H), 1.00 (t, 3H).

Example 17

2-butyl-3-[6-(1-ethoxycarbonylcyclopentyl)pyridin-3-ylmethyl]-5-chloro-3H-imidazole-4-carboxylic acid (83)

Step 1. 2-butyl-3-[6-(1-ethoxycarbonylcyclopentyl)pyridin-3-ylmethyl]-5-chloro-3H-imidazole-4-carboxylic acid ethyl ester (82)

Alkylation was carried out on 1-(5-bromomethylpyridin-2-yl)cyclopentane-carboxlic acid ethyl ester (45) as described in Example 1, Step 5, using 2-butyl-5-chloro-3H-imidazole-4-carboxylic acid ethyl ester (69) to produce the title compound (82).

¹H-NMR (CDCl₃): 8.30 (s, 1H), 7.25 (d, 2H), 5.55 (s, 2H), 4.30 (q, 2H), 4.10 (q, 2H), 2.65 (t, 2H), 2.50 (bm, 2H), 2.15 (bm, 2H), 1.70 (bm, 6H), 1.40 (m, 2H), 1.35 (t, 3H), 1.15 (t, 3H), 0.90 (t, 3H).

Step 2. 2-butyl-3-[6-(1-ethoxycarbonylcyclopentyl)pyridin-3-ylmethyl]-5-chloro-3H-imidazole-4-carboxylic acid (83)

Hydrolysis was performed on the product of Step 1, above (82), as described in Example 1, Step 6, to yield the title compound (83).

¹H-NMR (MeOD-d4): 8.25 (s, 1H), 7.45 (d, 1H), 7.35 (d, 1H), 5.65 (s, 2H), 2.70 (t, 2H), 2.05 (bm, 2H), 1.85 (bm, 2H), 1.70 (bm, 4H), 1.55 (m, 2H), 1.30 (m, 2h), 0.85 (t, 3H).

Example 18

2,5-dibutyl-4-[5-(1-carboxycyclopent-3-enyl)thiophen-2-ylmethyl]-2H-pyrazole-3-carboxylic acid (87)

Step 1. 1-(5-[2-(ethoxycarbonylmethoxyiminomethyl)-3-hydroxyhept-2-enyl]thiophen-2-yl)cyclopent-3-ene carboxylic acid ethyl ester (84)

To a solution of 1-(5-chloromethylthiophen-2-yl)cyclopent-3-ene carboxylic acid ethyl ester (5) (515 mg, 1.91 mM) and 2-methoxyimino-4-oxooctanoic acid ethyl ester (85) (428 mg, 1.91 mM) (prepared as described in patent application WO 915479) in 5.0 ml of DMF at room temperature was added K₂CO₃ (394 mg, 2.86 mM) and the reaction mixture was stirred for 24 hours, diluted with EtOAc, washed with water, saturated NaHCO₃ solution, saturated NaCl solution and dried over MgSO₄. The organic layer was filtered, concentrated to dryness and chromatographed on silica gel using 10% EtOAc in hexanes as the eluant to yield the title compound (84) (200 mg).

¹H-NMR (250 MHz, CDCl₃): 6.68 (d, 1H), 6.55 (d, 1H), 5.70 (s, 2H), 4.25 (q, 2H), 4.16 (q, 2H), 4.05 (s, 3H), 3.5 (dd, 1H), 3.4 (d, 2H, J=14 Hz), 3.14 (dd, 1H), 2.76 (d, 2H), J=14 Hz), 2.30 (t, 3H), 1.5 (m, 2H), 1.25 (m, 8H), 0.88 (t, 3H).

Step 2. 2,5-dibutyl-4-[5-(1-ethoxycarbonylcyclopent-3-enyl)thiophen-2-ylmethyl]-2H-pyrazole-3-carboxylic acid ethyl ester (86)

The product of Step 1, above (84) (100 mg, 0.22 mM), n-butylhydrazine oxalate (178 mg, 1.00 mM), 2.0 ml of acetic acid and 1.0 ml of 2-methoxyethanol were combined and heated to 120° C. for 48 hours. The solvents were evaporated from the reaction mixture and the resulting residue was diluted in CHCl₃, washed with 2N NaOH, dried over MgSO₄ and filtered. The filtrate was then concentrated to dryness and the material chromatographed on silica gel using 10% EtOAc in hexanes as the eluant to obtain the title compound (86) (50 mg).

¹H-NMR (CDCl₃): 6.65 (d, 1H), 6.45 (d, 1H), 5.70 (s, 2H), 4.50 (q, 2H), 4.30 (q, 2H), 4.15 (q, 2H), 4.10 (s, 2H), 3.30 (d, 2H), 2.75 (d, 2H), 2.55 (t, 2H), 1.75 (m, 2H), 1.55 (m, 2H), 1.35 (m, 4H), 1.25 (t, 3H), 1.20 (t, 3H), 0.95 (t, 3H), 0.90 (t, 3H).

Step 3. 2,5-dibutyl-4-[5-(1-carboxycyclopent-3-enyl)thiophen-2-ylmethyl]-2H-pyrazole-3-carboxylic acid (87)

The product of Step 2, above (86) (40 mg), was dissolved in 1.0 ml of methanol and an excess of 2N NaOH (0.5 ml) was added. The reaction mixture was stirred at room temperature for 5 hours, evaporated to dryness and the residue taken up into water. The aqueous solution was extracted with ethyl acetate to remove unreacted starting material, then was acidified with acetic acid and extracted again with ethyl acetate. The EtOAc extract was dried and concentrated using heptane to azeotrope off any residual acetic acid. The resulting solid was precipitated from EtOAc/hexanes, filtered and dried under vacuum to yield the title compound (87).

$^1$H-NMR (CDCl$_3$): 6.75 (d, 1H), 6.45 (d, 1H), 5.75 (s, 2H), 4.50 (t, 2H), 4.15 (s, 2H), 3.35 (d, 2H), 2.85 (d, 2H), 2.55 (t, 2H), 1.80 (m, 2H), 1.50 (m, 2H), 1.30 (m, 4H), 0.90 (t, 3H), 0.85 (t, 3H).

Example 19

5-butyl-4-|5-(1-carboxycyclopent-3-enyl)thiophen-2-ylmethyl|-2-trifluoromethyl-2H-pyrazole-3-carboxylic acid (89)

Step 1. 5-butyl-4-|5-(1-ethoxycarbonylcyclopent-3-enyl)thiophen-2-ylmethyl|-2-trifluoromethyl-2H-pyrazole-3-carboxylic acid ethyl ester (88)

1-(5-|2-(Ethoxycarbonylmethoxyiminomethyl)-3-hydroxyhept-2-enyl|thiophen-2-yl)cyclopent-3-ene carboxylic acid ethyl ester (84) was treated with 2,2,2-trifluoroethylhydrazine oxalate as described in Example 18, Step 2 to yield the title compound (88).

$^1$H-NMR (CDCl$_3$): 6.65 (d, 1H), 6.45 (d, 1H), 5.70 (s, 2H), 5.20 (q, 2H), 4.35 (q, 2H), 4.15 (s, 2H), 4.13 (q, 2H), 3.30 (d, 2H), 2.75 (d, 2H), 2.55 (t, 2H), 1.55 (m, 2H), 1.35 (m, 2H), 1.33 (t, 3H), 1.20 (t, 3H), 0.85 (t, 3H).

Step 2. 5-butyl-4-|5-(1-carboxycyclopent-3-enyl)thiophen-2-ylmethyl|-2-trifluoromethyl-2H-pyrazole-3-carboxylic acid (89)

Hydrolysis was carried out on the product of Step 1, above (88) as described in Example 18, Step 3, to obtain the title compound (89), m.p. 134°–135° C.

$^1$H-NMR (MeOD-d4): 6.65 (d, 1 H), 6.45 (d, 1 H), 5.65 (s, 2H), 5.35 (q, 2H), 4.20 (s, 2H), 3.25 (d, 2H), 2.65 (d, 2H), 2.50 (t, 2H), 1.50 (m, 2H), 1.30 (m, 2H), 0.85 (t, 3H).

Example 20

5-butyl-4-[5-(1-carboxycyclopent-3-enyl)thiophen-2-ylmethyl]-2-propyl-2H-pyrazole-3-carboxylic acid (91)

Step 1. 5-butyl-4-[5-(1-ethoxycarbonylcyclopent-3-enyl)thiophen-2-ylmethyl]-2-propyl-2H-pyrazole-3-carboxylic acid ethyl ester (90)

1-(5-[2-(Ethoxycarbonylmethoxyiminomethyl)-3-hydroxyhept-2-enyl]thiophen-2-yl)cyclopent-3-ene carboxylic acid ethyl ester (84) was treated with n-propylhydrazine oxalate as described in Example 1 8, Step 2, to yield the title compound (90).

$^1$H-NMR (CDCl$_3$): 6.70 (d, 1H), 6.50 (d, 1H), 5.70 (s, 2H), 4.45 (t, 2H), 4.30 (q, 2H), 4.12 (s, 2H), 3.30 (d, 2H), 2.75 (d, 2H), 2.60 (t, 2H), 1.80 (m, 2H), 1.55 (m, 2H), 1.30 (m, 2H), 1.28 (t, 3H), 1.25 (t, 3H), 0.95 (t, 3H), 0.90 (t, 3H).

Step 2. 5-butyl-4-[5-(1-carboxycyclopent-3-enyl)thiophen-2-ylmethyl]-2-propyl-2H-pyrazole-3-carboxylic acid (91)

Hydrolysis was performed on the product of Step 1, above (90), as described in Example 18, Step 3, to yield the title compound (91), m.p. 121°–122° C.

$^1$H-NMR (CDCl$_3$): 6.75 (d, 1H), 6.45 (d, 1H), 5.75 (s, 2H), 4.45 (t, 2H), 4.15 (s, 2H), 3.35 (d, 2H), 2.80 (d, 2H), 2.55 (t, 2H), 1.85 (m, 2H), 1.55 (m, 2H), 1.30 (m, 2H), 0.90 (m, 6H).

Example 21

1-|5-(2-butyl-5-methyl-4-oxo-4H-quinazolin-3-ylmethyl)thiophen-2-yl|cyclopent-3-ene carboxylic acid (109)

Step 1. 1-[5-(2-butyl-5-methyl-4-oxo-4H-quinazolin-3-ylmethyl)thiophen-2-yl|cyclopent-3-ene carboxylic acid ethyl ester (108)

Alkylation was carried out on 1-(5-chloromethylthiophen-2-yl)cyclopent-3-ene carboxylic acid ethyl ester (5) as described in Example 1, Step 5, using 2-butyl-6-methyl-3H-quinazolin-4-one (105) to produce the title compound (108).

$^1$H-NMR (CDCl$_3$): 8.05 (s, 1H), 7.55 (d, 2H), 6.85 (d, 1H), 6.75 (d, 1H), 5.65 (s, 2H), 5.40 (s, 2H), 4.15 (q, 2H), 3.30 (d, 2H), 2.90 (q, 2H), 2.80 (d, 2H), 2.50 (s, 3H), 1.80 (m, 2H), 1.50 (m, 2H), 1.20 (t, 3H), 1.00 (t, 3H).

Step 2. 1-|5-(2-butyl-5-methyl-4-oxo-4H-quinazolin-3-ylmethyl)thiophen-2-yl|cyclopent-3-ene carboxylic acid (109)

Hydrolysis was performed on the product of Step 1, above (108), as described in Example 1, Step 6, to yield the title compound (109), m.p. 150°–151° C.

$^1$H-NMR (MeOD-d4): 8.00 (s, 1H), 7.65 (d, 1H), 7.55 (d, 1H), 6.85 (d, 1H), 6.80 (d, 1H), 5.65 (s, 2H), 5.45 (s, 2H), 3.30 (d, 2H), 2.90 (t, 2H), 2.65 (d, 2H), 2.50 (s, 3H), 1.75 (m, 2H), 1.45 (m, 2H), 0.95 (t, 3H).

Example 22

1-[5-(2-butyl-5-methyl-4-oxo-4H-quinazolin-3-ylmethyl)pyridin-2-yl]cyclopentane carboxylic acid (111)

Step 1. 1-|5-(2-butyl-5-methyl-4-oxo-4H-quinazolin-3-ylmethyl)pyridin-2-yl]cyclopentane carboxylic acid ethyl ester (110)

Alkylation was carried out on 1-(5-bromomethylpyridin-2-yl)cyclopentane-carboxlic acid ethyl ester (45) as described in Example 1, Step 5, using 2-butyl-6-methyl-3H-quinazolin-4-one (105) to yield the title compound (110).

$^1$H-NMR (CDCl$_3$): 8.45 (s, 1H), 8.05 (s, 1H), 7.55 (d, 2H), 7.50 (d, 1H), 7.25 (d, 1H), 5.40 (s, 2H), 4.10 (q, 2H), 2.75 (t, 2H), 2.52 (bm, 2H), 2.50 (s, 3H), 2.15 (bm, 2H), 1.75 (bm, 4H), 1.20 (m, 2H), 1.15 (t, 3H), 0.95 (t, 3H).

Step 2. 1-[5-(2-butyl-5-methyl-4-oxo-4H-quinazolin-3-ylmethyl)pyridin-2-yl]cyclopentane carboxylic acid (111)

Hydrolysis was performed on the product of Step 1, above (110), as described in Example 1, Step 6, to produce the title compound (111).

$^1$H-NMR (MeOD-d4): 8.35 (s, 1H), 8.00 (s, 1H), 7.65 (d, 1H), 7.55 (d, 2H), 7.30 (d, 1H), 5.45 (s, 2H), 2.80 (t, 2H), 2.50 (s, 3H), 2.05 (bm, 2H), 1.70 (bm, 8H), 1.40 (m, 2H), 0.90 (t, 3H).

Example 23

1-[2-(2-ethyl-5,7-dimethylimidazo[4,5-b]pyridin-3-ylmethyl)pyrimidin-5-yl]cylopent-3-ene carboxylic acid Step 1. ethyl 2-methoxymethyl-4-hydroxypyrimidine-5-acetate Sodium metal (0.754 mol) was dissolved in absolute ethanol (100 ml) and the resulting solution was added dropwise to a solution of methoxyacetamidine hydrochloride (0.703 mol) in ethanol (100 ml). After 15 minutes the reaction mixture was filtered and the filtrate was added to a solution of diethyl formylsuccinate (0.703 mol), which was prepared according to H. Nakao et al. *Ann. Sankyo Res. Lab.*, 18, 33–37 (1966). The reaction was refluxed for 15 hours, cooled to room temperature and was then concentrated to obtain a crude solid. This solid was crystallized from isopropanol to obtain the title compound (43% yield), m.p. 142°–143° C.

$^1$H NMR (CDCl$_3$): 7.85 (s, 1H), 4.4 (s, 2H), 4.2 (q, J=7.5 Hz, 2H), 3.5 (s, 3H), 3.4 (s, 2H), 1.2 (t, J=7.5 Hz, 3H).

Step 2. ethyl-2-methoxymethyl-4-chloropyrimidine-5-acetate

A mixture of the product of Step 1, above (0.01 mol) and phosphorous oxychloride (7 ml) was refluxed for 20 minutes. The excess phosphorous oxychloride was removed, the residue was quenched with ice water (15 ml) and the mixture was extracted with ethyl acetate (2×20 ml). The ethyl acetate layer was collected and washed with water (2×10 ml). The organic extract was collected, dried over $MgSO_4$ and the dried portion was evaporated to obtain the title compound as an oil (78% yield).

$^1$H-NMR ($CDCl_3$): 8.58 (s, 1H), 4.65 (s, 2H), 4.17 (q, J=7 Hz, 2H), 3.72 (s, 2H), 3.52 (s, 3H), 1.24 (t, J=7 Hz, 3H).

Step 3. ethyl 2-methoxymethylpyrimidine-5-acetate

A mixture of the product of Step 3, above (1.6 mmol), palladium-carbon (5 mg), ethanol (30 ml) and ammonium hydroxide (28%, 2 ml) was hydrogenated in a Paar apparatus at a pressure of 43 pounds/inch$^2$ for 1 hour. The mixture was filtered and the filtrate was evaporated to a residue, which was partitioned between methylene chloride (20 ml) and water (10 ml). The methylene chloride layer was collected, washed with water and the organic extract was dried over $MgSO_4$. Evaporation of the dried methylene chloride layer gave the title compound (73% yield).

$^1$H-NMR ($CDCl_3$): 8.67 (s, 2H), 4.70 (s, 2H), 4.2 (q, J=8 Hz, 2H), 3.53 (s, 3H), 3.40 (s, 2H), 1.24 (t, J=8 Hz, 3H).

Step 4. 1-(2-methoxymethylpyrimidin-5-yl)cyclopent-3-ene carboxylate

A solution of the product of Step 3, above (42.8 mmol) in THF was cooled to −78° C. and to this was added a 1M solution of potassium t-butoxide in THF (47.1 ml) over 20 minutes so that the temperature of the reaction was maintained below −65° C. After 15 minutes at −65° C., cis-1,4-dichlorobut-2-ene (4.95 ml) was added dropwise and the reaction was maintained at −65° C. for 1 hour. A second portion of potassium t-butoxide in THF (47.1 ml) was added and the reaction was warmed to room temperature and quenched with saturated ammonium chloride solution. The solvents were removed in vacuo and the residue taken up in EtOAc and washed with water. The organic layer was washed with saturated sodium chloride and dried over $MgSO_4$. The residue obtained upon evaporation of EtOAc was chromatographed over silica gel using 25% EtOAc in hexanes as the eluent to obtain the title product (48% yield).

$^1$H-NMR ($CDCl_3$): 8.7 (s, 2H), 5.75 (s, 2H), 4.65 (s, 2H), 4.25 (q, J=7.5 Hz, 2H), 3.5 (s, 3H), 3.35 (d, J=14.6 Hz, 2H), 2.7 (d, J=14.6 Hz, 2H), 1.25 (t, J=7.5 Hz, 3H).

Step 5. ethyl 1-(2-hydroxymethylpyrimidin-5-yl)cyclopent-3-ene carboxylate

To a solution of the product of Step 4, above (19.5 mmol) in methylene chloride (20 ml) cooled to −78° C. was added boron tribromide (21.4 mmol) dissolved in methylene chloride (10 ml) over 15 minutes. The reaction was warmed to room temperature and quenched with water (5 ml). The methylene chloride layer was collected, washed with saturated sodium bicarbonate solution and dried over $MgSO_4$. Evaporation of methylene chloride gave the title compound (94% yield).

$^1$H-NMR ($CDCl_3$): 8.7 (s, 2H), 5.8 (s, 2H), 4.8 (s, 2H), 4.1 (q, J=7.5 Hz, 2H), 3.4 (d, J=16.5 Hz, 2H), 2.7 (d, J=16.5 Hz, 2H), 1.2 (t, J=7.5 Hz, 3H).

Step 6. ethyl 1-[2-(2-ethyl-5,7-dimethylimidazo[4,5-b]pyridin-3-ylmethyl)pyrimidin-5-yl]cyclopent-3-ene carboxylate To a solution of triphenylphosphine (4 mmol) in toluene (25 ml) was added di-t-butylazodicarboxylate (4 mmol) and the reaction was stirred for 15 minutes. At this time the product of Step 5, above (3.2 mmol) was added and the reaction was quenched with 5% hydrochloric acid (25 ml) after 6 hours. The aqueous layer was collected, washed with ether (2×20 ml), the acidic aqueous layer was neutralized with saturated sodium bicarbonate and extracted with EtOAc (2×20 ml). The EtOAc extract was dried over $MgSO_4$ and evaporated to dryness. The residue was chromatographed over silica gel using EtOAc as the eluent to obtain the title product (59% yield).

$^1$H-NMR ($CDCl_3$): 8.57 (s, 2H), 6.85 (s, 1H), 5.73 (s, 2H), 5.65 (s, 2H), 4.1 (q, J=7.5 Hz, 2H), 3.35 (d, J=14.6 Hz, 2H), 2.77 (q, J=7.5 Hz, 2H), 2.66 (d, J=14.6 Hz, 2H), 2.6 (s, 3H), 2.53 (s, 3H), 1.3 (t, J=7.5 Hz, 3H), 1.19 (t, J=7.5 Hz, 3H).

Step 7. 1-[2-(2-ethyl-5,7-dimethylimidazo[4,5-b]pyridin-3-ylmethyl)pyrimidin-5-yl]cyclopent-3-ene carboxylic acid Hydrolysis was performed on the product of Step 6, above, as described in Example 1, Step 6, to obtain the title compound (56% yield), m.p. 199°–200° C.

$^1$H-NMR ($CDCl_3$): 8.65 (s, 2H), 6.89 (s, 1H), 5.76 (s, 2H), 5.69 (s, 2H), 3.43 (m, 4H), 2.69 (d, J=14.6 Hz, 2H), 2.58 (s, 3H), 2.53 (s, 3H), 1.07 (t, J=7.5 Hz, 3H).

Example 24

1-[2-(2-cyclopropyl-5,7-dimethylimidazo[4,5-b]pyridin-3-ylmethyl)pyrimidin-5-yl]cyclopent-3-ene carboxylic acid Step 1. 1-(2-chloromethylpyrimidin-5-yl)cyclopent-3-ene carboxylic acid ethyl ester To a solution of ethyl 1-(2-hydroxymethylpyrimidin-5-yl)cyclopent-3-ene carboxylate (5.0 g, 20.1 mmol), in chloroform (50 ml) was added pyridine (5.1 ml), followed by thionyl chloride (4.4 ml, 60.3 mmol). The reaction mixture was refluxed for 30 minutes, cooled to room temperature and quenched with water (50 ml). The chloroform layer was collected, washed successively with saturated sodium bicarbonate solution and saturated sodium chloride solution. The organic extract was dried over $MgSO_4$ and then evaporated to an oily residue, which was purified by flashe chromatography with hexanes/ethyl acetate (3:1) as eluent.

$^1$H-NMR ($CDCl_3$): 8.7 (s, 2H), 5.75 (s, 2H), 4.7 (s, 2H), 4.2 (q, J=7.5 Hz, 2H), 3.4 (d, J=16.5 Hz, 2H), 2.6 (d, J=16.5 Hz, 2H), 1.2 (t, J=7.5 Hz, 3H).

Step 2. 1-[2-(2-cyclopropyl-5,7-dimethylimidazo[4,5-b]pyridin-3-ylmethyl)pyrimidin-5-yl]cyclopent-3-ene carboxylic acid ethyl ester Alkylation was carried out on the product of Step 1, above, as described in Example 1, Step 5.

$^1$ H-NMR ($CDCl_3$): 8.54 (s, 2H), 6.83 (s, 1 H), 5.76 (m, 2H), 5.74 (m, 2H), 4.11 (q, J=7.5 Hz, 2H), 3.36 (d, J=14.7 Hz, 2H), 2.67 (d, J=14.7 Hz, 2H), 2.56 (s, 3H).

Step 3. 1-[2-(2-cyclopropyl-5,7-dimethylimidazo[4,5-b]pyridin-3-ylmethyl)pyrimidin-5-yl]cyclopent-3-ene carboxylic acid Hydrolysis was performed on the product of Step 2, above, as described in Example 1, Step 6, yielding the title compound, m.p. 203°–204° C.

$^1$H-NMR ($CDCl_3$): 8.7 (s, 2H), 6.88 (s, 1H), 5.75 (s, 2H), 5.74 (s, 2H), 3.25 (d, J=14.8 Hz, 2H), 2.72 (d, J=14.8 Hz, 2H), 2.46 (s, 3H), 2.42 (s, 3H), 2.10 (m, 1H), 1.0 (m, 2H), 0.91 (m, 2H).

Example 25

1-[5-(2-cyclopropyl-5,7-dimethylimidazo[4,5-b]pyridin-3-ylmethyl)thiophen-2-yl]cyclopenten-3-ene carboxylic acid benzenesulfonamide A mixture of 1-[5-(2-cyclopropyl-5,7-dimethylimidazo[4,5-b]pyridin-3-ylmethyl)thiophen-2-yl]cyclopenten-3-ene

37 carboxylic acid (Example 3) (500 mg, 1.27 mmol) and 1,1-carbonyl diimidazole (250 mg, 1.27 mmol) in THF (25 ml) was heated under reflux for 3 hours, then a solution of benzenesulfonamide (242 mg, 1.6 mmol) and DBU (243 mg, 1.6 mmol) in THF (2.0 ml) was added. The reaction mixture was heated at 40° C. for 19 hours, cooled to 23° C. and concentrated in vacuo. The residue was dissolved in water and acidified with 10% aqueous $NaH_2PO_3$. The aqueous mixture was extracted with EtOAc (3×25 ml). The combined extracts were dried and concentrated in vacuo. The crude residue was chromatographed on $SiO_2$ gel using 2% MeOH/EtOAc to give 406 mg of the title compound (60% yield).

$^1$H-NMR (300 MHz, MeOH): 7.7 (d, 2H), 7.4 (t, 1H), 7.26 (t, 2H), 6.96 (s, 1H), 6.85 (d, 1H), 6.64 (d, 1H), 5.68 (s, 2H), 5.60 (s, 2H), 3.25 (d, J=17 Hz, 2H), 2.62 (d, J=17 Hz, 2H), 2.58 (s, 3H), 2.53 (s, 3H), 2.18 (m, 1H), 1.1 (m, 4H).

Example 26

1-[5-(2-cyclopropyl-5,7-dimethylimidazo[4,5-b] pyridin-3-ylmethyl)thiophen-2-yl]cyclopenten-3-ene carboxylic acid p-toluenesulfonamide The title compound was prepared from the product of Example 3, Step 6, above, by the method of Example 25, except that p-toluenesulfonamide was used in place of benzenesulfonamide.

$^1$H-NMR (300 MHz, MeOH): 7.65 (d, 2H), 7.18 (d, 2H), 6.95 (s, 1H), 6.8 (d, 1H), 6.55 (d, 1H), 5.68 (s, 2H), 5.60 (s, 2H), 3.17 (d, J=17 Hz, 2H), 2.65 (d, J=17 Hz, 2H), 2.58 (s, 3H), 2.55 (s, 3H), 2.35 (s, 3H), 2.20 (m, 1H), 1.10 (m, 4H).

Example 27

1-[5-(2-cyclopropyl-5,7-dimethylimidazo[4,5-b] pyridin-3-ylmethyl)thiophen-2-yl]cyclopenten-3-ene carboxylic acid methanesulfonamide The title compound was prepared from the product of Example 3, above, by the method of Example 25, except that methanesulfonamide was used in place of benzenesulfonamide.

$^1$H-NMR (300 MHz, MeOH): 6.95 (s, 1H), 6.85 (d, 1H), 6.78 (d, 1H), 5.68 (s, 2H), 5.62 (s, 2H), 3.25 (d, 2H), 2.9 (bs, 1H), 2.65 (d, J=16.5 Hz, 1H), 2.57 (s, 3H), 2.51 (s, 3H), 2.2 (m, 1H), 1.10 (m, 4H).

Example 28

1-[5-(2-cyclopropyl-5,7-dimethylimidazo[4,5-b] pyridin-3-ylmethyl)thiophen-2-yl]cyclopenten-3-ene carboxylic acid trifluoromethanesulfonamide The title compound was prepared from the product of Example 3, by the method of Example 25, except that trifluoromethanesulfonamide was used in place of benzenesulfonamide.

$^1$H-NMR (300 MHz, MeOH): 6.96 (s, 1H), 6.82 (d, 1H), 6.78 (d, 1H), 5.70 (s, 2H), 5.62 (s, 2H), 3.3 (d, 2H), 2.65 (d, J=17 Hz, 2H), 2.6 (s, 3H), 2.55 (s, 3H), 2.2 (m, 1H), 1.1 (m, 4H).

38

We claim:
1. A compound having the structure

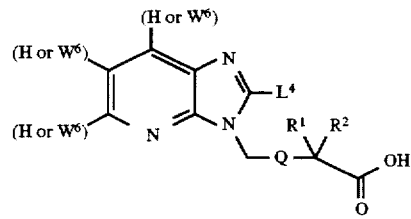

wherein:
Q is

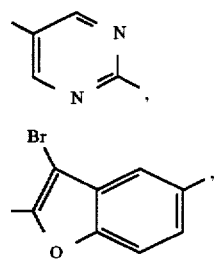

thienyl, pyridyl, naphthyl or benzofuryl;

$L^4$ is $C_1$ to $C_4$ alkyl or $C_3$ to $C_5$ cycloalkyl;

each $W^6$ is independently $C_1$ to $C_6$ alkyl, amino, $C_1$ to $C_6$ alkylamino, di($C_1$ to $C_6$)alkylamino, acylamino or diacylamino; and $R^1$ an $R^2$ are taken together and form cyclopentane, cyclohexane, cyclopentene, tetrahydropyran or indan.

2. A compound according to claim 1 selected from:
1-[5-(2-ethyl-5,7-dimethylimidazo[4,5-b]pyridin-3-ylmethyl)thiophen-2-yl]cyclopent-3-ene carboxylic acid;
1-[5-(5,7-dimethyl-2-propylimidazo[4,5-b] pyridin-3-ylmethyl)thiophen-2-yl]cyclopent-3-ene carboxylic acid;
1-[5-(2-cyclopropyl-5,7-dimethylimidazo[4,5-b]pyridin-3-ylmethyl)thiophen-2-yl]cyclopent-3-ene carboxylic acid;
1-[5-(2-cyclopropyl-5,7-dimethylimidazo[4,5-b]pyridin-3-ylmethyl)thiophen-2-yl]cyclopentane carboxylic acid;
4-[5-(2-ethyl-5,7-dimethylimidazo[4,5-b] pyridin-3-ylmethyl)thiophen-2-yl]tetrahydropyran-4-carboxylic acid;
2-[5-(2-ethyl-5,7-dimethylimidazo[4,5-b]pyridin-3-ylmethyl)thiophen-2-yl]indan-2-carboxylic acid;
2-[5-(2-cyclopropyl-5,7-dimethylimidazo[4,5-b]pyridin-3-ylmethyl)thiophen-2-yl]indan-2-carboxylic acid;
1-[5-(2-ethyl-5,7-dimethylimidazo[4,5-b]pyridin-3-ylmethyl)thiophen-2-yl]cyclohexane carboxylic acid; and
1-[5-(2-cyclopropyl-5,7-dimethylimidazo[4,5-b]pyridin-3-ylmethyl)thiophen-2-yl]cyclohexane carboxylic acid.

3. The compound according to claim 2 which is 1-[5-(2-cyclopropyl-5,7-dimethylimidazo[4,5-b]pyridin-3-ylmethyl)thiophen-2-yl]cyclopent-3-ene carboxylic acid.

4. A compound according to claim 1 selected from:
1-[5-(2-ethyl-5,7-dimethylimidaz[4,5-b]pyridin-3-ylmethyl)pyridin-2-yl]cyclopentane carboxylic acid;
1-[5-(2-cyclopropyl-5,7-dimethylimidazo[4,5-b]pyridin-3-ylmethyl)pyridin-2-yl]cyclopentane carboxylic acid;
1-[2-(2-ethyl-5,7-dimethylimidazo[4,5-b]pyridin-3-ylmethyl)pyrimidin-5-yl]cyclopent-3-ene carboxylic acid;
1-[2-(2-cyclopropyl-5,7-dimethylimidazo[4,5-b]pyridin-3-yl)pyrimidin-5-yl]cyclopent-3-ene carboxylic acid;

1-|6-(2-ethyl-5,7-dimethylimidazo|4,5-b|pyridin-3-ylmethyl)naphthalen-2-yl|cyclopent-3-ene carboxylic acid; and 1-|3-bromo-5-(2-ethyl-5,7-dimethylimidazo|4,5-b|pyridin-3-ylmethyl)benzofuran-2-yl|cyclopentane carboxylic acid.

5. A compound having the structure

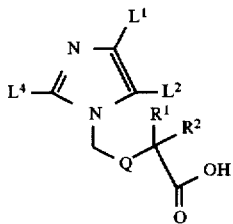

wherein:

Q is

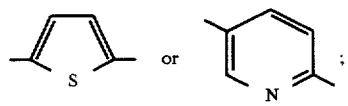

$L^1$ and $L^2$ are taken separately and are each independently halo, $C_1$ to $C_6$ alkyl or —$CO_2H$;

$L^4$ is $C_1$ to $C_4$ alkyl; and $R^1$ and $R^2$ are taken together and are —$CH_2CH_2CH_2CH_2$— or —$CH_2CH=CHCH_2$—.

6. A compound according to claim 5 selected from:

2-butyl-3-[5-(1-carboxycyclopent-3-enyl)thiophen-2-ylmethyl]-5-chloro-3H-imidazole-4-carboxylic acid;

3-[5-(1-carboxycyclopent-3-enyl)thiophen-2-ylmethyl]-5-ethyl-2-propyl-3H-imidazole-4-carboxylic acid; and 3-|5-(1-Carboxycyclopent-3-enyl)thiophen-2-ylmethyl]-5-chloro-2-propyl-3H-imidazole-4-carboxylic acid.

7. A compound according to claim 1 selected from:

1-[5-(2-cyclopropyl-5,7-dimethylimidazo[4,5-b]pyridin-3-ylmethyl)thiophen-2-yl]cyclopenten-3-ene carboxylic acid benzenesulfonamide;

1-[5-(2-cyclopropyl-5,7-dimethylimidazo[4,5-b]pyridin-3-ylmethyl)thiophen-2-yl]cyclopenten-3-ene carboxylic acid p-toluenesulfonamide;

1-|5-(2-cyclopropyl-5,7-dimethylimidazo|4,5-b|pyridin-3-ylmethyl)thiophen-2-yl|cyclopenten-3-ene carboxylic acid methanesulfonamide; and 1-|5-(2-cyclopropyl-5,7-dimethylimidazo|4,5-b|pyridin-3-ylmethyl)thiophen-2-yl|cyclopenten-3-ene carboxylic acid trifluoromethanesulfonamide.

8. A pharmaceutical composition comprising a therapeutically effective amount of a compound according to claim 1 or 5 or a pharmaceutically acceptable salt thereof, and a pharmaceutically acceptable carrier.

9. 1-Thiophen-2-yl-cyclopent-3-ene carboxylic acid ($C_1$ to $C_4$ alkyl) ester;

1-(5-formylthiophen-2-yl)cyclopent-3-ene carboxylic acid ($C_1$ to $C_4$ alkyl) ester;

1-(5-chloromethylthiophen-2-yl)cyclopent-3-ene carboxylic acid ($C_1$ to $C_4$ alkyl) ester; or 1-|5-(2-ethyl-5,7-dimethylimidazo|4,5-b|pyridin-3-ylmethyl)thiophen-2-yl|cyclopent-3-ene carboxylic acid ($C_1$ to $C_4$ alkyl) ester; wherein said alkyl is optionally substituted with one or more substituents independently selected from halo, nitro and cyano.

10. A method of inhibiting the effects of angiotension II in a mammal comprising administering to said mammal an angiotension II-inhibiting amount of a compound according to claim 1 or 5 or a pharmaceutically acceptable salt thereof.

11. A method of treating hypertension in a mammal comprising administering to said mammal a blood pressure-lowering amount of a compound according to claim 1 or 5 or a pharmaceutically acceptable salt thereof.

12. A method of treating glaucoma, renal disease or cognitive dysfunction in a mammal comprising administering to said mammal a therapeutically effective amount of a compound according to claim 1 or 5 or a pharmaceutically acceptable salt thereof.

13. A compound according to to claim 9 wherein said alkyl is ethyl.

* * * * *